United States Patent
Liu et al.

(10) Patent No.: US 8,445,533 B2
(45) Date of Patent: May 21, 2013

(54) ANDROGRAPHOLIDE DERIVATIVES TO TREAT VIRAL INFECTIONS

(75) Inventors: Rui Hai Liu, Ithaca, NY (US); James R. Jacob, Cortland, NY (US); Bud Tennant, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 922 days.

(21) Appl. No.: 11/269,942

(22) Filed: Nov. 8, 2005

(65) Prior Publication Data

US 2006/0223785 A1    Oct. 5, 2006

Related U.S. Application Data

(60) Provisional application No. 60/626,253, filed on Nov. 8, 2004, provisional application No. 60/626,172, filed on Nov. 8, 2004, provisional application No. 60/728,978, filed on Oct. 21, 2005, provisional application No. 60/626,329, filed on Nov. 8, 2004.

(51) Int. Cl.
*A61K 31/34*    (2006.01)

(52) U.S. Cl.
USPC ................................................. 514/473

(58) Field of Classification Search
USPC ................................................. 514/473
See application file for complete search history.

(56) References Cited

U.S. PATENT DOCUMENTS

| | | | |
|---|---|---|---|
| 6,140,063 A | 10/2000 | Wheelock et al. | |
| 2002/0016363 A1 | 2/2002 | Nanduri et al. | |

FOREIGN PATENT DOCUMENTS

| | | | |
|---|---|---|---|
| CN | 1293955 A | | 5/2001 |
| CN | 1433756 A | * | 8/2003 |
| CN | 1433757 A | | 8/2003 |
| CN | 1433758 A | | 8/2003 |
| CN | 1437939 A | | 8/2003 |
| CN | 1450059 A | | 10/2003 |
| CN | 1478774 A | | 3/2004 |
| CN | 1554337 A | | 12/2004 |
| WO | WO 96/17605 A1 | * | 6/1996 |
| WO | 01/57026 A1 | | 8/2001 |
| WO | 01/85710 A1 | | 11/2001 |

OTHER PUBLICATIONS

Puri et al. "Immunostimulant agents from Andrographis paniculata," J. Nat. Prod. 1993, vol. 56, No. 7, pp. 995-999.*
Rice, Fields Virology, Third Eddition, 1995, pp. 931-933.*
Ding et al. CN 1433756 abstract, CAPLUS Accession No. 2005:327819.*
Machine translation of CN 1433756A.*
Basak et al., "Inhibition of Proprotein Convertases-1, -7 and Furin by Diterpines of Andrographis Paniculata and Their Succinoyl Esters," Biochem. J. 338:107-13 (1999).
Supplementary European Search Report for European Patent Application No. EP05857736 (Dec. 15, 2009).
Tomassini et al., "An in Vitro Flaviviridae Replicase System Capable of Authentic RNA Replication," Virology 313:274-85 (2003).

(Continued)

*Primary Examiner* — Shengjun Wang
(74) *Attorney, Agent, or Firm* — LeClairRyan, a Professional Corporation

(57) ABSTRACT

The present invention provides a methods and compositions for treating a host afflicted with a viral infection, particularly a Flaviviridae infection, including hepatitis C infection, comprising administering an effective antiviral amount of a derivative of andrographolide alone or in combination or alternation with another antiviral compound.

2 Claims, 13 Drawing Sheets

OTHER PUBLICATIONS

XP002560446, Database WPI Week 200430, Thomson Scientific, London, GB; AN 2004-317044 (Printed Dec. 12, 2009).

International Search Report for International Patent Application No. PCT/US05/40716 (Apr. 2, 2007).

Schuppan et al., "Herbal Products for Liver Diseases: A Therapeutic Challenge for the New Millennium," Hepatology 30(4):1099-1104 (1999).

Wiart et al., "Antiviral Properties of Ent-labdene Diterpenes of Andrographis paniculata Nees, Inhibitors of Herpes Simplex Virus Type 1," Phytother. Res. 19:1069-1070 (2005).

Written Opinion of the International Searching Authority for International Patent Application No. PCT/US05/40716 (Feb. 26, 2007).

Basak, A., "Inhibitors of Proprotein Convertases," J. Mol. Med. 83:844-855 (2005).

Basak et al., "Implication of the Proprotein Convertases Furin, PC5 and PC7 in the Cleavage of Surface Glycoproteins of Hong Kong, Ebola and Respiratory Syncytlal Viruses: A Comparative Analysis With Fluorogenic Peptides," Biochem. J. 353:537-545 (2001).

Jiang et al., "Synthesis and Evaluation of Antibacterial Activities of Andrographolide Analogues," European J. Med. Chem. 44:2936-2943 (2009).

Jada et al., "Semisynthesis and In Vitro Anticancer Activities of Andrographolide Analogues," Phytochemistry 68:904-912 (2007).

Chang et al., Pharmacology and Applications of Chinese Materia Medica, vol. II, World Scientific 917-918 (1987).

Jacobson et al. "Pharmacokinetics, Safety, and Antiviral Effects of Hypericin, a Derivative of St. John's Wort Plant, in Patients with Chronic Hepatitis C Virus Infection," Antimicrob. Agents and Chemother. 45(2): 517-524 (2001).

Japanese Patent Office Notice of Reasons for Rejection (Translation) for Corresponding Japanese Patent Application No. 2007-540206 (mailed Dec. 15, 2011).

\* cited by examiner

EFFECT OF DIFFERENT COMPOUNDS ON PRODUCTION OF MITOCHONDRIAL DNA AND LACTIC ACID ON HepG2 CELLS

| COMPOUND | [], µM | [], µg/mL | TOTAL LA* PRODUCTION (µg/µL) | PERCENTAGE OF mDNA PRODUCTION | NORMALIZED LA PRODUCTION (%) | CONCLUSION |
|---|---|---|---|---|---|---|
| NO DRUG | 10 | | 1.39 | 100.0 | 100 | |
| DDC | 10 | | 0.96 | 0.4 | 19240 | INCREASED |
| 3TC | 10 | | 1.50 | 110.9 | 97 | NORMAL |
| (+)-BCH-189 | 100 | | 0.41 | 0.1 | 40028 | INCREASED |
| MTI-3 | | 10 | 1.64 | 157.8 | 75 | NORMAL |
| | | 1 | 1.62 | 115.6 | 101 | NORMAL |
| | | 0.1 | 1.55 | 98.6 | 113 | NORMAL |
| LA*, LACTIC ACID | | | | | | |

| COMPOUND, [ ] | Huh.2a | | | Huh.8b | | | Ava.1c | | | Clone Bd | | |
|---|---|---|---|---|---|---|---|---|---|---|---|---|
| | EC90 | EC50 | CC50 | EC90 | EC50 | CC50 | EC90 | EC50 | CC50 | EC90 | EC50 | CC50 |
| MTI-3, µg/ml | <0.1 | <0.1 | >10 | <0.1 | <0.1 | >10 | 0.4 | <0.1 | >10 | 0.8 | <0.1 | 91.3 |
| C-021, µg/ml | NDe | ND | ND | ND | ND | ND | ND | ND | ND | 0.7 | <0.1 | >10 |
| 2'-MeC ANALOG, µM | 8.7 | 0.7 | >10 | 10.3 | 5.4 | >10 | 7.1 | 0.5 | >10 | 8.8 | 2.9 | >100 |

*FIG. 10*

ANDROGRAPHOLIDE DERIVATIVES TO TREAT VIRAL INFECTIONS

CROSS-REFERENCE TO RELATED APPLICATIONS

This application claims priority to U.S. Provisional application No. 60/626,253 entitled "Andrographolide Derivatives to Treat Flaviviruses and Pestiviruses", filed Nov. 8, 2004, U.S. Provisional Application Nos. 60/626,172, filed Nov. 8, 2004 and 60/728,978, filed Oct. 21, 2005, both entitled "Andrographolide Derivatives to Treat Hepatitis C" and U.S. Provisional Application No. 60/626,329, entitled "Andrographolide Derivatives as Protease Inhibitors", filed Nov. 8, 2004.

FIELD OF THE INVENTION

The present invention includes andrographolide derivatives, and their pharmaceutical compositions and methods of use for the treatment of Flaviviridae infections, other viral infections and to inhibit viral proteases.

BACKGROUND OF THE INVENTION

Hepacivirus (HCV), pestiviruses and flaviviruses belong to the Flaviviridae family of viruses (Rice, C. M., Flaviviridae: The viruses and their replication. In: Fields Virology, Editors: Fields, B. N., Knipe, D. M., and Howley, P. M., Lippincott-Raven Publishers, Philadelphia, Pa., Chapter 30, 931-959, 1996).

Hepatitis C virus (HCV) is the leading cause of chronic liver disease worldwide. HCV is known to cause at least 80% of post transfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (HBV). A small proportion of healthy persons appear to be chronic HCV carriers, varying with geography and other epidemiological factors. HCV encodes two proteases, a zinc-dependent metalloproteinase, encoded by the NS2-NS3 region, and a serine protease encoded in the NS3 region. These proteases are required for cleavage of specific regions of the precursor polyprotein into mature peptides.

The current standard of care for the treatment of HCV is treatment with interferon or a combination of interferon and ribavirin, although numerous compounds are in clinical trials for other anti-HCV treatments.

Several patents disclose protease inhibitors for the treatment of HCV. U.S. Pat. No. 6,004,933 to Spruce et al. discloses a class of cysteine protease inhibitors for inhibiting HCV. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor.

Extracts of plants have also been used to treat HCV infections. For example, U.S. Pat. No. 6,056,961 discloses extracts of the plant *Hypericum perforatum* and pharmaceutical compositions thereof for the treatment of HCV infection. Other U.S. patents disclosing plant extracts for the treatment of HCV infection include: U.S. Pat. No. 5,837,257 to Tsai et al., U.S. Pat. No. 5,725,859 to Omer et al.

The pestivirus genus includes bovine viral diarrhea virus (BVDV), classical swine fever virus (CSFV, also called hog cholera virus) and border disease virus (BDV) of sheep. Moennig V., et al, *Adv. Vir. Res.* 41:53-98 (1992). Pestivirus infections of domesticated livestock (cattle, pigs, and sheep) cause significant economic losses worldwide (Meyers, G. and Thiel, H.-J., *Advances in Virus Research*, 47, 53-118, 1996; Moennig V., et al, *Adv. Vir. Res.* 41:53-98, 1992).

The flavivirus genus includes more than 68 members separated into groups on the basis of serological relatedness (Calisher et al., *J. Gen. Virol.* 70:3743, 1993). Clinical symptoms vary and include fever, encephalitis, and hemorrhagic fever (*Fields Virology*, Editors: Fields, B. N., Knipe, D. M., and Howley, P. M., Lippincott-Raven Publishers, Philadelphia, Pa., Chapter 31, 931-959, 1996). Flaviviruses of global concern that are associated with human disease include the dengue hemorrhagic fever viruses (DHF), yellow fever virus, shock syndrome, and Japanese encephalitis virus (Halstead, S. B., *Rev. Infect. Dis.* 6:251-264, 1984; Halstead, S. B., *Science*, 239:476-481, 1988; Monath, T. P., *New Eng. J. Med.*, 319:641-643, 1988).

The current standard of care for treatment of Flaviviridae infection is limited to treatment with interferon or a combination of interferon and ribavirin.

One strategy in treating viral infections has been the targeting of viral proteases, which are essential components in the replication of some viruses. Proteases are enzymes, such as pepsin or trypsin, that catalyze the hydrolysis of a protein. The hydrolysis can result in an active protein or a completely processed protein. Alternatively, proteases can simply degrade the protein completely. A nonlimiting list of viruses that encode proteases include: Retroviridae, Picornaviridae, Herpesviridae, Flaviviradae, Coronaviridae, and Togaviridae. The focus on viral proteases has generated significantly effective treatments for viral infections, perhaps most notably in the treatment of viral infections and the success using them in the treatment of human immunodeficiency virus (HIV) infection. Use of protease inhibitors in combination with reverse transcriptase inhibitors is now a preferred treatment for HIV infection.

Protease inhibitors are described in the patent literature. For example, U.S. Pat. No. 6,114,312 discloses and claims a method of inhibiting HIV by combined use of hydroxyurea, a nucleoside analog, and a protease inhibitor. U.S. Pat. No. 5,872,210 to Medabalimi claims and discloses transfrarne peptide inhibitors of viral protease. U.S. Pat. No. 5,945,413 to Tung et al. discloses and claims compounds that inhibit aspartyl proteases. U.S. Pat. No. 6,100,277 to Tucker et al. discloses and claims methods of treating retroviral infections by administering combinations of protease inhibitors.

Piconavirues are one of the largest families of medically important human pathogens and are the major cause of human diseases such as poliomyelitis, acute hepatitis, myocarditis, and the common cold (Wang, Q. M. (1999) Progress In Drug Research 52:199-219). Picornaviruses are small non-enveloped RNA viruses and encode the 3C protease on a single polycistronic mRNA. Enteroviruses and human rhinoviruses are picornaviruses that encode an additional protease, the 2A protease. The viral 2A and 3C proteases are classified as cysteine proteases. The 3C protease has been the target of antiviral agents because it is present in all members of the picornavirus family and makes multiple cleavages on the polyprotein precursor. The catalytic site of the 3C protease is composed of His-Glu-Cys.

Inhibitors of 3C protease can be peptidic or non-peptidic. Peptidic inhibitors include peptide aldehyde and Michael acceptor derivatives. Non-peptidic protease inhibitors include small molecules containing reactive carbonyl groups. Examples of non-peptidic protease inhibitors include β-lactams, isatins, homophthalimides, naphthoquinone-lactol, quinone-like citrinin hydrate, radicinin, and triterpene sulfates (Wang, Q. M. (1999) Progress In Drug Research 52:199-2 19). All but triterpene sulfates inactivate the 3C protease active site nucleophile. Protease inhibitors have been described for treatment of picrornavirus (see U.S. Pat. No. 5,821,331 to Hammond et al. describing compounds and methods for making peptidyl-aldehydes as anti-pircornaviral agents).

Members of the Herpesviridae family of viruses include cytomegalovirus (CMV), herpes simplex virus type 1 (HSV-1), and herpes simplex virus type 2 (HSV-2). Herpesviridae members encode a serine protease that plays an essential role in virus capsid maturation making the protease essential for replication. The CMV capsid protease assemblin contains Ser-His-His in its active site. Benzoxazinone compounds and monocyclic β-lactams have been reported to inhibit assemblin (Abood, N. A. et al. (1997) Bioorg Med. Chem. Lett. 7:2105-2108; Collier, A. C. et al. (1996) N. Engl. J. Med 334:1011-1017). Peptidic inhibitors have also been reported (Patick, A. K. and K. E. Potts (1998) Clinical Microbiology Reviews 11:614-627). U.S. Pat. Nos. 6,008,033 and 6,083,711 to Abdel-MegUid et al. discloses novel herpes protease crystalline structures and methods of identifying inhibitors of these proteases.

The Coronaviridae family includes human respiratory coronavirus and other large, enveloped, plus strand RNA viruses. These viruses cause highly prevalent diseases in humans and animals. Both viral and host proteases process the primary translation product from a polycistronic mRNA. The coronavirus infectious bronchitis virus encodes a trypsin-like protease with His and Cys residues in the catalytic center (Ng, L. F. et al. (2000) Virology 272(1):27-39). A cysteine protease, papain-like protease (PL1pro), of the human coronavirus 229E (HCoV) regulates the expression of the replicase polyproteins, pp1a and ppa1ab, by cleavage between Gly111 and Asn112, far upstream of its own catalytic residue Cys1054 (Herold, J. et al. (1999) J Biol Chem 274(21):14918-25).

Togaviridae include alphaviruses and rubiviruses. Sinbis and Semliki Forest virus are examples of alphaviruses, and rubella virus is the sole member of the rubivirus genus. These viruses are enveloped, plus RNA viruses. Many can be transmitted by mosquitoes. In alphaviruses the genomic RNA serves as the mRNA which is translated into a polyprotein that is co- and posttranslationally cleaved to yield four polypeptides, nsP1, nsP2, nsP3, and nsP4. nsP2 has been identified has containing the protease activity responsible for this cleavage. In the Sinbis virus, the nsPs are translated as two polyproteins, P123 and P1234. P1234 is cleaved at the 3/4 site to yield P123 and nsP4 which is the complex thought to initiate minus-strand synthesis. P123 is cleaved to produce nsP 1, nsP2, and nsP3 which together with nsP4 form the complexes to perform plus-strand RNA synthesis (Schlesinger, S. and M. J. Sclesinger, Togaviridae: The viruses and their replication. in: Fields Virology, Editors: Fields, B. N., Knipe, D. M., and Howley, P. M., Lippincott Raven Publishers, Philadelphia, Pa., Chapter 27, 825-842, 1996) Thus protease activity is critical in Togaviridae replication.

It is an object of the present invention to provide methods and compositions for the treatment of Flaviviridae infection.

It is a specific object of the present invention to provide methods and compositions for the treatment of HCV infection.

It is another object of the present invention to provide methods and compositions for the treatment of flavivirus and pestivirus infections.

It is another object of the present invention to provide methods and compositions for the inhibition of viral proteases.

SUMMARY OF THE INVENTION

It has now been discovered that one can treat a host infected with a Flaviviridae virus, including either a flavivirus, pestivirus or hepatitis C, by administering an effective amount of a derivative of andrographolide of the structure:

or its cis isomer, or its pharmaceutically acceptable salt, ester or prodrug; wherein the variables are defined below in the Detailed Description of the Invention. In another embodiment, any of the compounds herein can be used to treat other viral infections. In yest another embodiment, the compounds are useful as protease inhibitors. In a principle embodiment, the compounds are provided as a mixture of at least two andrographolide derivatives as described herein.

It should be understood that the anti-viral activity of the compounds may or may not be based on or derived from protease activity. The anti-viral compounds may be acting through other viral enzymes or pathways, for example, through a polymerase activity.

Injectable extracts of *Andrographis paniculata* that include certain esters of andrographolide have been established to be safe to humans and have been used for a variety of medicinal properties. However, prior to the present invention, it was unknown that derivatives of andrographolide are effective against flavivirus, pestivirus or hepatitis C. In one embodiment the efficacy of the compound is determined by measuring the reduction of viral-induced cell killing and the reduction in viral yields. In preferred embodiments the compound exhibits an $EC_{50}$ of less than 25, 15, 10, 5, or 1 micromolar. In one embodiment, the viral protease is not an HIV protease.

In another embodiment, the active compound can be administered in combination or alternation with another antiviral, anti-pestivirus, anti-flavivirus anti-HCV agent, or an anti-protease agent. In combination therapy, an effective dosage of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Nonlimiting examples of compounds that can be used in combination with the andrographolide derivatives are lipoic acid and n-acetyl cysteine.

BRIEF DESCRIPTION OF THE FIGURES

FIG. 10 is a chart of the EC50, EC90 and CC50 of compounds MTI-3, C-021 (a succinic acid ester of andrographolide referred to as DASM (dehydroandrographolide succinic acid monooester)) and 2'-MeC is B-D-2'-methylcytidine.

DETAILED DESCRIPTION OF THE INVENTION

Figure 1:
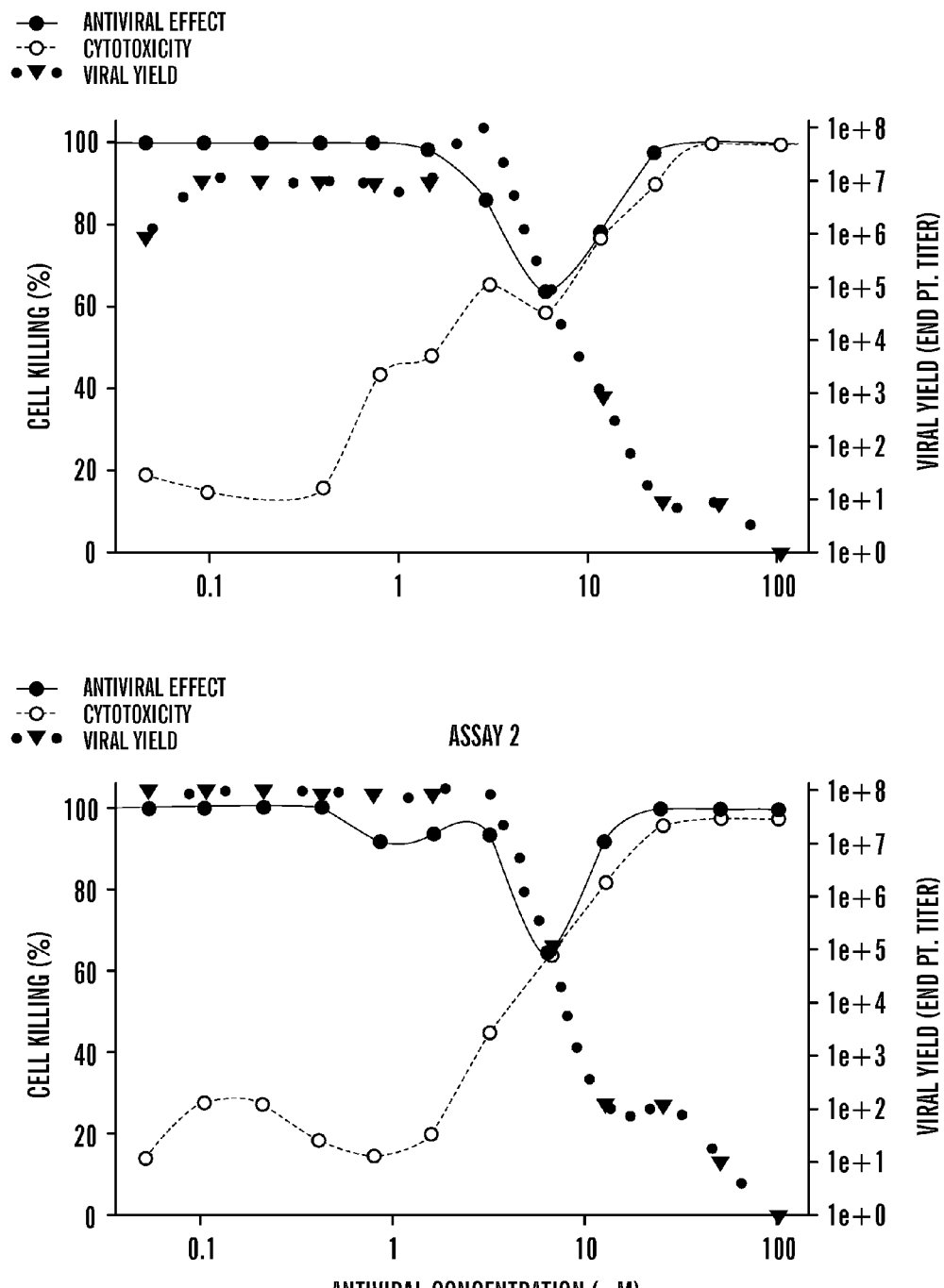
FIG. 1 is a set of line graphs demonstrating the effect of ribavirin on BVDV cell killing and viral yield after infection of bovine cells. NCL cells were plated at a density of $2 \times 10^4$ cells/well (0.38 cm$^2$) and half the culture plate was inoculated with cpBVDV (m.o.i.=0.01). Infected and uninfected cells were treated with ribavirin over a range of 100-0.049 µM for 3 days, followed by methylene blue assay to measure cell numbers. Cell killing (%)=[(cell number in uninfected, untreated controls) (cell numbers after BVDV infection with drug treatment or drug treatment alone)]÷(total number of cells in uninfected, untreated controls) at day 3 of assay. Viral yield from BVDV infected cells with drug treatment were determined by infecting fresh cultures with serial 10-fold dilutions of medium collected on day 3 of assay. An end-point titer was measured by methylene blue assay 5 days after infection. Results of two independently run experiments are shown. A peak, log normal, 4 parameter equation was used to calculate the Ribavirin concentration which had the maximal effect on reduction of cell killing due to BVDV infection. A sigmoidal, logistic, 4 parameter equation was used to calculate the Ribavirin concentration at which 50% of uninfected cells were killed and the drug concentration which reduced viral titers by 90%. These values are listed in Table 1 found in the specification.

The present invention is a method, compound and composition for treating a host infected with a Flaviviridae virus, including either a flavivirus, pestivirus or hepatitis C, another viral infection that includes administering an effective amount of a derivative of andrographolide of the formula:

or its cis isomer, or its pharmaceutically acceptable salt, ester, salt of an ester or prodrug as further defined below. In an alternative embodiment, the compound can be used to inhibit a protease such as a viral protease. Certain of the andrographolide derivatives are known and others are new.

I. Background on Extracts of *Andrographis paniculata*

*Andrographis paniculata* is an annual herb in the acanthus family that is extensively used in medicine as a bitter tonic, febrifuge and for bowel complaints (Glossary of Indian Medicinal Plants, Ed. R. N. Chopra, S. L. Nayar, I. C. Chopra, p 18, 1996. The useful plants of India, Ed. By S. B. Ambasta, p 39, 1992). The plant has also been shown to be antithrombotic (Chinese Medical Journal 1991, 104 (9), p 770-775) and inhibit stenosis and restenosis after angioplasty in the rat (Chinese Medical Journal, 1994, 107 (6), p 464-470). Preliminary results also indicate that it can significantly alleviate atherosclerotic iliac artery stenosis induced by both deendothelialization and high cholesterol diet and restenosis following angioplasty in rabbits (Wang, D. W. et al. *Chin. Med. J. (Engl)* 107:464-470, 1994).

Significant attention has been paid by several research groups on *A. paniculata* in recent years due to its cytotoxic, antitumorogenic, cell differentiation inducing activities and anti-HIV activities. WO 96/17605 discloses that the methanol extract of *Andrographis paniculata* down regulates p34 cdc2 and acts as a kinase inhibitor. HIV-1 replication in vitro was reported to be inhibited by the methonal extract by inhibiting c-Mos. WO 96/17605 discloses and claims methods for inhibiting cyclins, c-Mos, and cellular kinases.

Alcohol extracts of *Andrographis paniculata* have also been reported to have immunostimulatory effects in mice (Pun, A. et al. *J. Nat. Prod.* 56:995-999, 1993). Extracts of *Andrographis paniculata* have also been reported as a successful treatment for tumors. Such extracts have been used to treat chorioepithelioma and chorioadenoma (Yin, J., and Guo, L. (1993) Contemporary Traditional Chinese Medicine Xie Yuan, Beijing). The methanol extract of the aerial parts of *A. paniculata* Nees showed potent cell differentiation inducing activity on mouse myeloid leukemia (M1) cells (Chem. Pharm. Bull. 1994, 42 (6) 1216-1225).

The plant has also been shown to be useful in the treatment of certain bacterial infections (Int. J. Crude Drug Res. 1990, 28 (4), p 273-283; Drugs of the Future. 1990, 15 (8) p 809-816).

It is also known that the plant extract and its constituents exhibit promising hepatoprotective activity (Planta Medica, 1987, 53 (2), p 135-140). Alcoholic extracts of *Andrographis paniculata* have been reported to prevent carbon tetrachloride-induced liver damage (Rana, A. C. et al. Arch. Pharm. Res. 14:93-95, 1991).

Extracts of *A. paniculata* are effective in treating certain viral infections. An extract of *Andrographis paniculata* has been reported to be effective to treat respiratory tract infections and viral pneumonia in China and is commercially available (Manufacturers Product Description Guide, Yi-Bin Pharmaceuticals, Wuliangye Co., LTD, Yibin, Sichuan, P. R. China). Extracts of *Andrographis paniculata* have also been reported to be effective in reducing the prevalence and intensity of the symptoms associated with the common cold (Caceres, D. D., et al. *Phytomedicine* 6:217-23, 1999) and have been reported to possess antimalarial effects (Rahman, N. N. A., et al. *J. Ethnopharmacol.* 64:249-54, 1999; Kapil, A. et al. *Biochem. Pharmacol.* 46:182-185, 1993, *Int. J. Pharmacognosy*, 1992, 30(4), p 263-274).

In International patent application WO91/01742, compositions containing one or more ingredients obtained from the plants *Valeariana officinalis* and/or *A. paniculata* were disclosed to have antiviral, antineoplastic, antibacterial and immunomodulatory activity.

The plant is also reported to inhibit proprotein convertases-1, -7 and furin, possibly by suppressing the proteolytic cleavage of envelope glycoprotein gp 160 of HIV (Biochem. J., 1999, 338, 107-113). However, aqueous extracts of *Andrographis paniculata* were reported to have little or no antiviral effect on HIV-1 activity. (Yao, X. J., et al. *Virology* 187:56-62, 1992). Yao et al. tested crude extracts of *Arctium lappa, Astragalus membraneaceus, Andrographis paniCulata*, and *Prunella vulgaris* for inhibitory effects of HIV-1. Only extracts of *P. vulgaris* demonstrated anti-HIV activity, and Yao et al. suggest that inhibition is achieved by preventing the binding of gp120 to CD4.

Furthermore, extracts of *Andrographis paniculata* have been reported to have little or no effect on hepatitis B surface antigen expression (Mehrotra, R. et al. *Indian J. Med. Res.* 92:133-138, 1990).

Andrographolide, an active constituent isolated from *Andrographis paniculata* was first isolated by Gorter (Rec. trav. chim., 1911, 30, p 1S1-160). Andrographolide is a diterpenoid lactone and is known to have the following naturally occurring analogs: 14-epiandrographolide isoandrographolide; 14-deoxy-12-methoxyandrographolide; 12-epi-14-12-methoxyandrographolide; 14-deoxy-12-hydroxyanthrographolide and 14-deoxy-11-hydroxyandrographolide. The chemical structure of andrographolide is illustrated belo

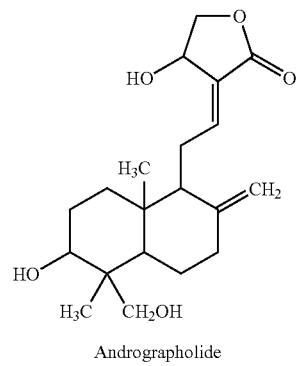 [SMILES: C=C1CCC2C(C)(CO)C(O)CCC2(C)C1C/C=C1/C(=O)OCC1O]

Andrographolide

Andrographolide was found to show significant cytotoxic activity against KB and P388 lymphocytic leukemia. However, andrographalide analogs 14-deoxy-11,12-didehydroandrographolide and neoandrographolide (formula IV & V) have shown no cytotoxic activity in tumor cell lines (J. Sci. Soc. Thailand, 1992, 18, 187-194).

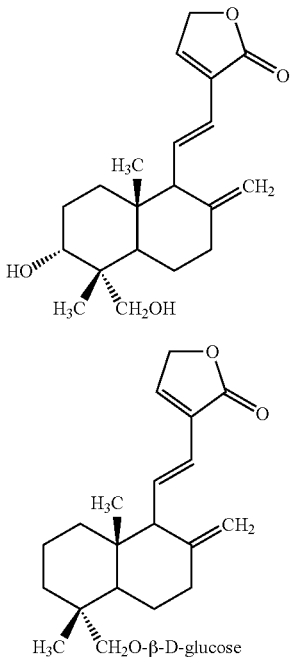

Similarly, Japanese patent application JP 63-88124, discloses a mixture of at least two compounds of formula VIa, VIb and describes their activity as antitumorogenic agents:

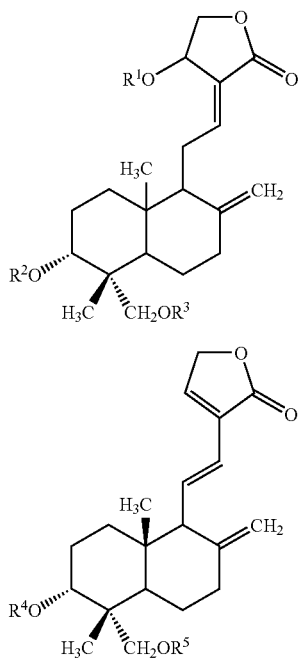

($R^1$, $R^2$, $R^3$, $R^4$ and $R^5$ are H or lower alkanoyl).

Andrographolide is also reported to have protective activity against paracetamol-induced toxicity on ex vivo preparations of isolated rat hepatocytes (Visen, P. K., et al. *J. Ethnopharmacol.* 40:13 1-136, 1993).

WO 01/85709 discloses derivatives of andrographolide, their stereoisomers, their polymorphs, their pharmaceutically acceptable salts, their pharmaceutically acceptable solvates, useful in the treatment of cancer, HSV, HIV, psoriasis, restonosis, atherosclerosis and other cardiovascular disorders, antiviral, antimalarial, antibacterial, hepatoprotective, immunomodulating agents and for treatment of metabolic disorders.

U.S. Pat. No. 5,833,994 discloses the use of aryl hydrocarbon receptor ligands in combination with andrographolide for the treatment of viral infections.

DASM (dehydroandrographolide succinic acid monoester) prepared from andrographolide of the formula II was found to inhibit HIV virus and to be nontoxic to the H9 cell at the concentrations of 50-200, ug/ml and was inhibitory to HIV-1 (IIIB) at the minimal concentration of 1.6-3.1 pg/ml (Chang, R. S. et al. Proc. Sco. Exp. Biol. Med. 197:59-66, 1991). Chang et al. report that DASM inhibits HIV growth by interfering with the binding of virions to cells and with a step in the viral replication cycle subsequent to virus-cell binding. Chang et al did not assay DASM for HIV protease inhibition. Basak, A. et al. *Biochem. J.* 338:107-13, 1999 report that, while succinoyl ester deriviatives of andrographolide inhibited proprotein convertase-1, -7 and funin, andrographolide itself demonstrated relatively little enzyme inhibition.

II. Active Compounds

The present invention is a method compound, and compostion for treating a host infected with a Flaviviridae virus, including either a flavivirus, pestivirus or hepatitis C by administering an effective amount of an andrographolide or its derivative of the formula:

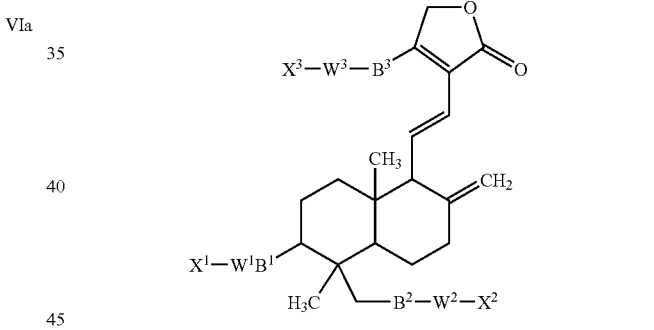

or its cis isomer, or its pharmaceutically acceptable salt, ester, salt of an ester or prodrug, wherein:

$B^1$, $B^2$ and $B^3$ are independently $CR^1R^2$, $C(Y^1)$, O, $NR^4$, $PR^5$, $P(=Y^2)R^6$, $P(=Y^3)_2$, $S(=Y^4)_k$, a spacer group or a covalent bond; and k can be 0, 1 or 2; and $W^1$, $W^2$ and $W^3$ are independently $CR^7R^8$, $CR^9$, C, $C(Y^5)$, O, $NR^{10}$, $PR^{11}$, $P(=Y^6)R^{12}$, $P(=Y^7)_2$, $S(=Y^8)_f$ or a covalent bond; and f can be 0, 1 or 2; or $B^1$—$W^1$, $B^2$—$W^2$, and/or $B^3$—$W^3$ are independently $CR^3$=$CR^9$ or C≡C; and $X^1$, $X^2$ and $X^3$ are independently hydrogen, $CR^{18}R^{19}R^{20}$, C=$R^{21}R^{22}$, C=$R^{23}$, C≡N, C(=$Y^9$)$R^{24}$, $OR^{25}$, $NR^{26}R^{27}$, N=$NR^{28}$, $P(=Y^{10})_d(R^{29})$V, $S(=Y^{11})_d(R^{30})_i$ or $NO_2$; and d can be 0, 1 or 2; and v can be 0, 1 or 2; and i can be independently 0 or 1; and $Y^1$, $Y^2$, $Y^3$, $Y^4$, $Y^5$, $Y^6$, $Y^7$, $Y^8$, $Y^9$, $Y^{10}$ and $Y^{11}$ are independently O, S or NZ; and Z can be independently hydrogen, $R^{13}$, $OR^{14}$, $SR^{15}$ or $NR^{16}R^{17}$; and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ are independently hydrogen, alkyl, alkenyl, alkynyl, cycloalkyl, cycloalkenyl, cycloalkynyl, aryl, alkaryl, arylalkyl, heterocyclic, heteroaromatic, acyl, aldehyde, carbamide, alkoxy, amino, halogen, silyl, thiol, sulfoxy, sulfinyl, sulfamoyl, hydroxyl, ester, carboxylic acid, amide, nitro, cyano, phosphonyl, phosphinyl, phosphoryl, imide, thioester, ether, acid halide, oxime, carbamate, thioether, residue of a natural or synthetic amino acid or a carbohydrate, any of which can be optionally attached to the targeting moiety or oxygen radical through a spacer group; or alternatively, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ can individually come together to form a bridged compound comprising of alkyl, alkenyl, alkynyl, cycloalkyl, cycloalkenyl, cycloalkynyl, aryl, alkaryl, aryl alkyl, heterocyclic, heteroaromatic, acyl, carbamide, alkoxy, amino, halogen, silyl, thiol, sulfinyl, sulfamoyl, ester, amide, phosphonyl, phosphinyl, phosphoryl, imide, thioester, ether, oxime, carbamate, thioether, residue of a natural or synthetic amino acid or a carbohydrate, any of which can be optionally attached to the targeting moiety or oxygen radical through a spacer group; and each carbon atom cannot be covalently bound to more than two heteroatoms; and wherein each B, W and X cannot be all heteroatom moieties unless B, W and X are all nitrogen based or B and X are independently O or N and W is $PR^{11}$, $POR^{12}$, $PO_2$, $S(Y^4)_m$ and m is 1 or 2; and wherein each B and W or W and X cannot both be of the general formula C(Y), $POR^{12}$, $PO_2$, $S(=Y^4)_t$ and t is 1 or 2.

In one subembodiment of formula I, $B^1$, $B^2$ and $B^3$ are independently $CR^1R^2$, $C(Y^1)$, O, or a covalent bond; $W^1$, $W^2$ and $W^3$ are independently $CR^7R^8$, $CR^9$, C, $C(Y^5)$, O, or a covalent bond; and $X^1$, $X^2$ and $X^3$ are independently hydrogen, $CR^{18}R^{19}R^{20}$, $C=R^{21}R^{22}$, $C\equiv R^{23}$.

In one subembodiment of formula I, at least one of $B^1$, $B^2$ and $B^3$ and at least one $W^1$, $W^2$ and $W^3$ is a covalent bond and at least one $X^1$, $X^2$ and $X^3$ is hydrogen.

In another embodiment of formula I, at least one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is selected from an aliphatic, saturated or unsaturated alkyl, alkenyl or alkynyl. In one subembodiment, the alkyl, alkenyl or alkynyl groups are substituted, and can be halogen substituted.

In one embodiment of formula I, at least one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is selected from a carbonyl containing groups, including, but not limited to, aldehyde, ketone, carboxylic acid, ester, amide, enone, acyl chloride or anhydride.

In one embodiment of formula I, at least one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is selected from an alkyl, aryl, heteroaryl or heteroaromatic ring.

In one embodiment of formula I, at leats one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is independently selected from alkyl or nitro.

In one embodiment of formula I, at least one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is independently selected from a phosphate.

In one embodiment of formula I, at least one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is independently selected from a sulfates and thiol.

In one embodiment of formula I, at least one $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ is independently selected from amine.

Andrographolide has a number of chiral carbon atoms (i.e., carbon atoms bound to four different substituents), and thus can exist in a number of different stereochemical configurations. A compound is referred to as "chiral" if it is not superimposable on its mirror image. Stereoisomers that are non-superimposable mirror images are called enantiomers or optical isomers. Optical isomers rotate a plane of polarised light in opposite directions. The effect of chirality is that the enantiomers have opposite spatial orientations. The enantiomers of a racemate are thus said to have "handedness" in that they resemble a set of human hands. A racemic compound is a 50:50 mixture of mirror image molecules (enantiomers). Stereoisomers that are not mirror images of each other are called diastereomers.

In one embodiment, the andrographolide derivative exhibits the stereochemistry as found in nature. In other embodiments, the andrographolide has non-naturally occurring stereochemistry, or is administered as a racemate.

In one embodiment, the invention provides a method, compound and composition for treatment of a host infected with a Flaviviridae virus, including either a flavivirus, pestivirus or hepatitis C, by administering an effective amount of a derivative or andrographolide of the formula:

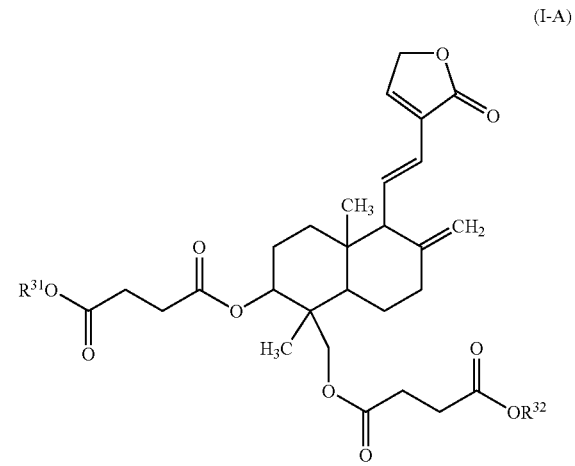

(I-A)

or its cis isomer, or its pharmaceutically acceptable salt, ester, salt of an ester or prodrug; wherein $R^{31}$ and $R^{32}$ are defined above.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

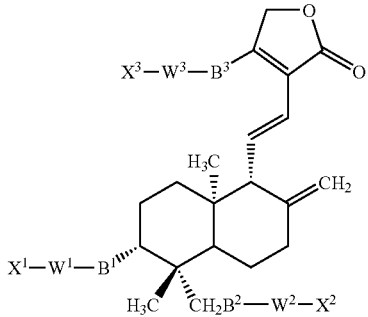

(I-B)

or its pharmaceutically acceptable salt, ester, salt of an ester or prodrug; wherein the substituents are as previously defined.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

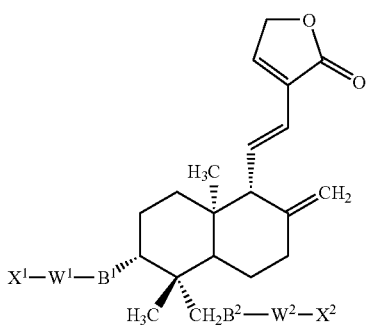

(I-C)

or its pharmaceutically acceptable salt, ester, salt of an ester or prodrug; wherein the substituents are as defined above.

In another embodiment, the invention a method, compound and composition for treatment of a host infected with a Flaviviridae virus, including either a flavivirus, pestivirus or hepatitis C, that includes administering an effective amount of a andrographolide or its derivative of the formula:

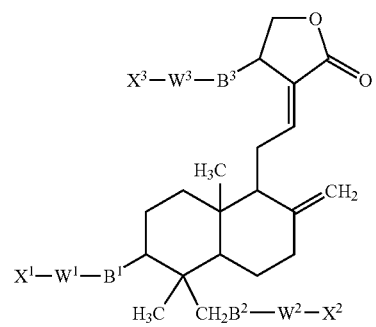

(II)

or its cis isomer, or its pharmaceutically acceptable salt, ester, salt of an ester or prodrug; wherein:

$B^1$, $B^2$ and $B^3$ are independently $CR^1R^2$, $C(Y)$, O, $NR^4$, $PR^5$, $P(=Y^2)R^6$, $P(=Y^3)_2$, $S(=Y^4)_k$, a spacer group or a covalent bond; and k can be 0, 1 or 2; and $W^1$, $W^2$ and $W^3$ are independently $CR^7R^8$, $CR^9$, C, $C(Y^5)$, O, $NR^{10}$, $PR^{11}$, $P(=Y^6)R^{12}$, $P(=Y^7)_2$, $S(=Y^8)_f$ or a covalent bond; and f can be 0, 1 or 2; or $B^1—W^1$, $B^2—W^2$, and/or $B^3—W^3$ are independently $CR^3=CR^9$ or $C≡C$; and $X^1$, $X^2$ and $X^3$ are independently hydrogen, $CR^{18}R^{19}R^{20}$, $C=R^{21}R^{22}$, $C=R^{23}$, $C≡N$, $C(=Y^9)R^{24}$, $OR^{25}$, $NR^{26}R^{27}$, $N=NR^{28}$, $P(=Y^{10})_d(R^{29})V$, $S(=Y^{11})_d(R^{30})_i$ or $NO_2$; and d can be 0, 1 or 2; and v can be 0, 1 or 2; and i can be independently 0 or 1; and $Y^1$, $Y^2$, $Y^3$, $Y^4$, $Y^5$, $Y^6$, $Y^7$, $Y^8$, $Y^9$, $Y^{10}$ and $Y^{11}$ are independently O, S or NZ; and Z can be independently hydrogen, $R^{13}$, $OR^{14}$, $SR^{15}$ or $NR^{16}R^{17}$; and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, and $R^{32}$ are independently hydrogen, alkyl, alkenyl, alkynyl, cycloalkyl, cycloalkenyl, cycloalkynyl, aryl, alkaryl, arylalkyl, heterocyclic, heteroaromatic, acyl, aldehyde, carbamide, alkoxy, amino, halogen, silyl, thiol, sulfoxy, sulfinyl, sulfamoyl, hydroxyl, ester, carboxylic acid, amide, nitro, cyano, phosphonyl, phosphinyl, phosphoryl, imide, thioester, ether, acid halide, oxime, carbamate, thioether, residue of a natural or synthetic amino acid or a carbohydrate, any of which can be optionally attached to the targeting moiety or oxygen radical through a spacer group; or alternatively, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ can individually come together to form a bridged compound comprising of alkyl, alkenyl, alkynyl, cycloalkyl, cycloalkenyl, cycloalkynyl, aryl, alkaryl, aryl alkyl, heterocyclic, heteroaromatic, acyl, carbamide, alkoxy, amino, halogen, silyl, thiol, sulfinyl, sulfamoyl, ester, amide, phosphonyl, phosphinyl, phosphoryl, imide, thioester, ether, oxime, carbamate, thioether, residue of a natural or synthetic amino acid or a carbohydrate, any of which can be optionally attached to the targeting moiety or oxygen radical through a spacer group; and each carbon atom cannot be covalently bound to more than two heteroatoms; and wherein B, W and X cannot be all heteroatom moieties unless B, W and X are all nitrogen based or B and X are independently O or N and W is $PR^{11}$, $POR^{12}$, $PO_2$, $S(Y^4)_m$ and m is 1 or 2; and wherein B and W or W and X cannot both be of the general formula $C(Y)$, $POR^{12}$, $PO_2$, $S(=Y^4)_t$ and t is 1 or 2.

In a further embodiment, the invention provides a method, compound and composition for treatment of a host infected with a Flaviviridae virus, including either a flavivirus, pestivirus or hepatitis C, administering an effective amount of a derivative or andrographolide of the formula:

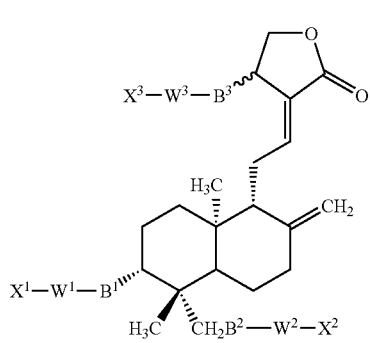
(II-A)

or its pharmaceutically acceptable salt, ester, salt of an ester or prodrug; wherein the substituents are as defined above.

In yet another embodiment, the invention provides a method, compound and composition for treatment of a host infected with a Flaviviridae virus, including either a flavivirus, pestivirus or hepatitis C, that includes administering an effective amount of a derivative or andrographolide of the formula:

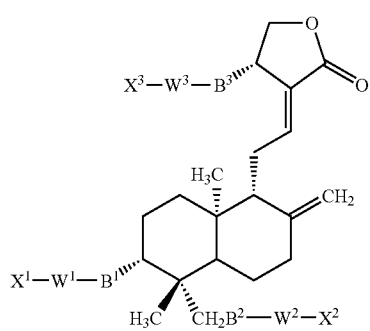
(II-B)

or its pharmaceutically acceptable salt, ester, salt of an ester or prodrug; wherein the substituents are as previously defined.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

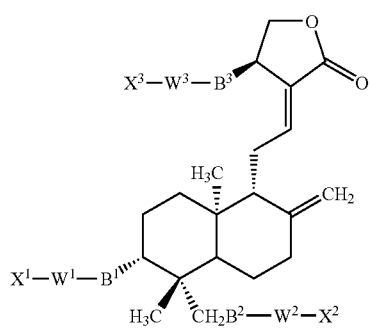
(II-C)

or its pharmaceutically acceptable salt, ester, salt of an ester or prodrug; wherein the substituents are as previously defined.

In yet another embodiment, the invention provides a method, compound and composition for treatment of a host infected with a Flaviviridae virus, including either a flavivirus, pestivirus or hepatitis C, that includes administering an effective amount of a derivative or andrographolide of the formula:

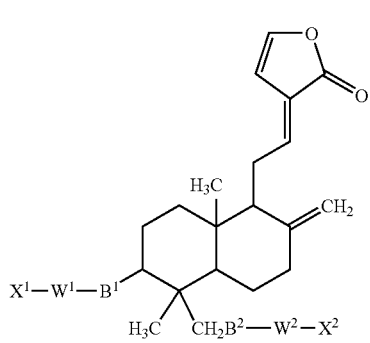
(III)

or its cis isomer, or its pharmaceutically acceptable salt, ester, salt of an ester or prodrug; wherein the substituents are as previously defined.

In yet another embodiment, the invention provides a method, compound and composition for treatment of a host infected with a Flaviviridae virus, including either a flavivirus, pestivirus or hepatitis C, that includes administering effective amount of a derivative or andrographolide of the formula:

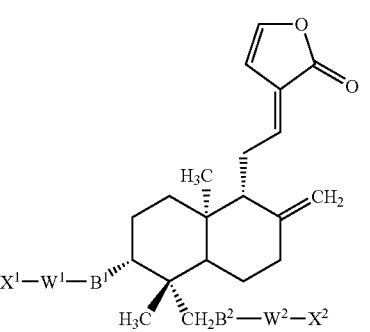
(III-A)

or its pharmaceutically acceptable salt, ester, salt of an ester or prodrug; wherein the substituents are as previously defined.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

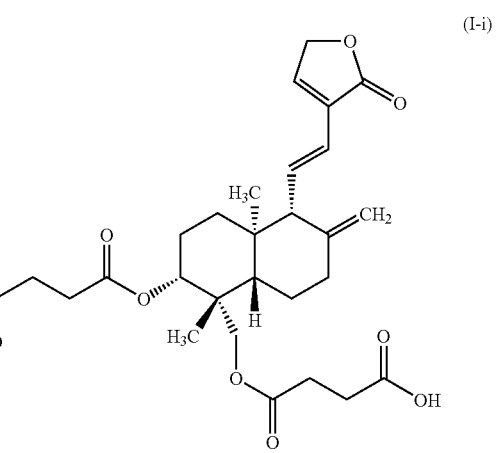
(I-i)

or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

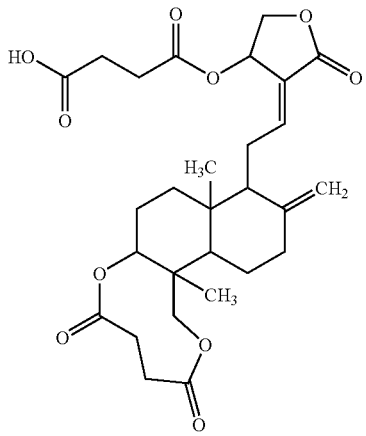

(II-i)

or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

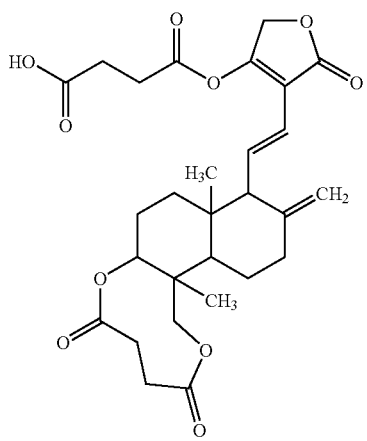

(I-ii)

or its cis isomer, or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

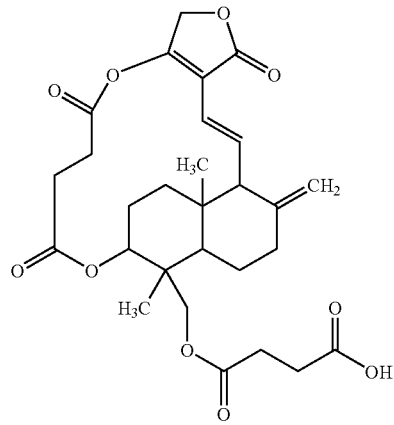

(I-iii)

or its cis isomer, or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

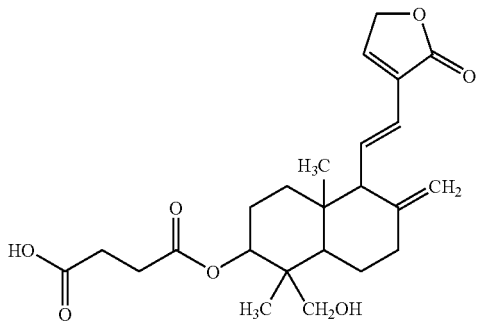

(I-iv)

or its cis isomer, or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

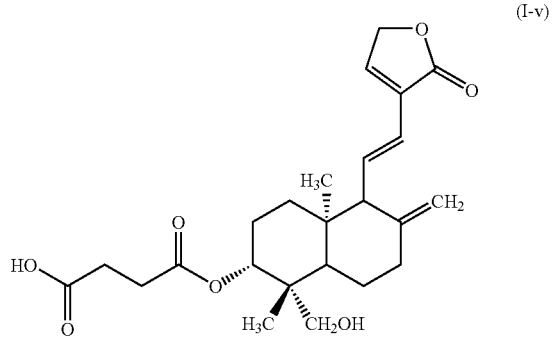 [SMILES: C=C1CCC2[C@@](C)(CC[C@@H](OC(=O)CCC(=O)O)[C@@]2(C)CO)C1/C=C/C1=CCOC1=O]

(I-v)

or its cis isomer, or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, that includes administering an effective amount of a derivative or andrographolide of the formula:

(I-vi)

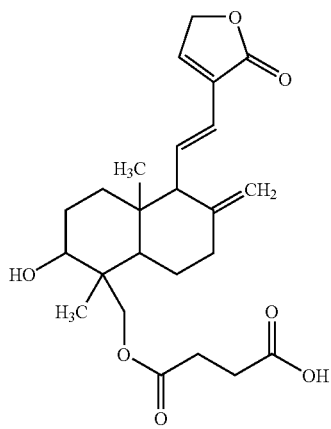

or its cis isomer, or its pharmaceutically acceptable salt, salt of an ester or prodrug.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

(I-vii)

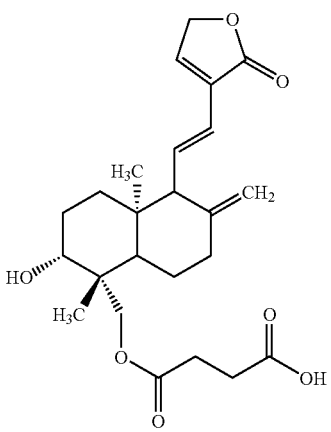

or its cis isomer, or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

(II-ii)

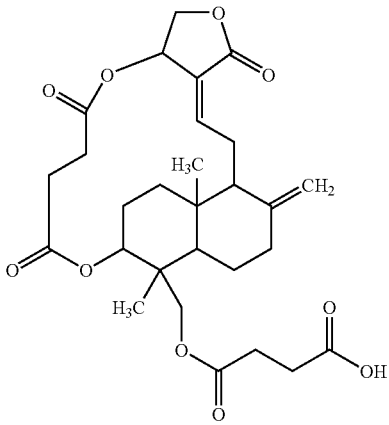

or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

(III-i)

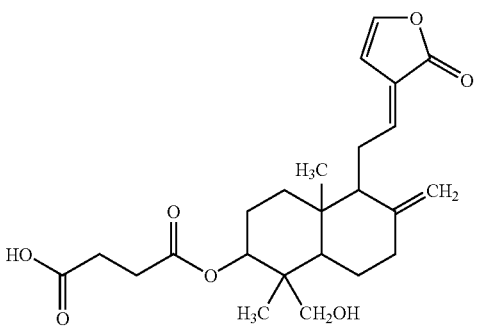

or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

(III-ii)

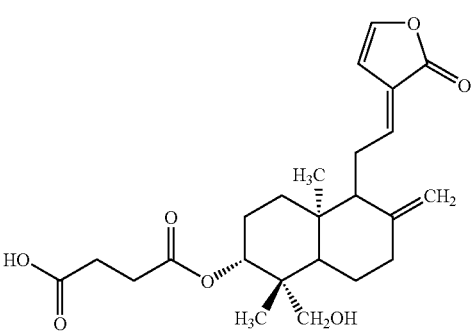

or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

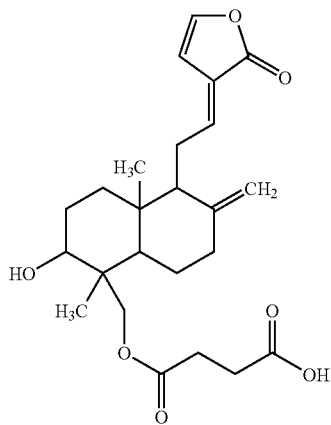

(III-iii)

or its pharmaceutically acceptable salt, ester, salt of an ester or prodrug.

In another embodiment, the invention provides a method, compound and composition for treatment of a host infected with a Flaviviridae virus, including either a flavivirus, pestivirus or hepatitis C, by administering an effective amount of a derivative or andrographolide of the formula:

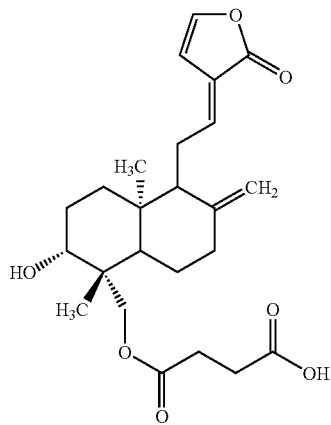

(III-iv)

or its pharmaceutically acceptable salt, ester, salt of an ester or prodrug.

In another embodiment, the andrographolide contains at least one ester group that includes a functional moiety which increases the water solubility of the compound over the parent andrographolide and that exhibits anti-Flaviviridae or anti-protease activity, including, but not limited to saturated and unsaturated dicarboxylic acids and salts thereof, amino carboxylic acids and salts thereof, aldehyde containing carboxylic acids and salts thereof, an amine group, a salt of an amine group, an amide group, aldehydes groups and the salts thereof. In yet another embodiment, the ester has a functional moiety selected from the group consisting of sulfonic acids, sulfonic acid esters, phosphoric acids, phosphoric acid esters, cyclic phosphates, polyhydroxyalkyl groups, carbohydrate group, C(O)-spacer-$SO_3H$, wherein spacer is —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S)$—, -(aryl-O)—, —(O-aryl)-, -(alkyl-O)—, —(O-alkyl)-; n is 0, 1, 2, 3, 4, 5, 6, 7, 8, 9, or 10; C(O)-spacer-$SO_3M$, wherein M is a metal used to form a pharmaceutically acceptable salt, for example, sodium or potassium, C(O)-spacer-$PO_3H_2$, C(O)-spacer-$PO_3M_2$, C(O)-spacer-$PO_3HM$, C(O)-spacer-$PO_4H$, C(O)-spacer-$PO_4M$, $SO_3M$, —$PO_3H_2$, —$PO_3M_2$, —$PO_3HM$, cyclic phosphates, polyhydroxyalkyl, carbohydrate groups, C(O)-spacer-$[O(C_{1-3}\text{alkyl})_p]_n$, wherein n is as defined above and p is 1, 2, or 3, —$[O(C_{1-3}\text{alkyl})_p]_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

In one principle embodiment, the method includes administration of at least two andrographolide derivatives as described herein in combination to a host for the treatment or prophylaxis of a viral infection, including a Flaviviridae infection. In certain embodiments, a mixture of at least three, at least four, or at least five andrographolide derivatives is administered. In certain embodiments, the andrographolide derivatives are in the form of salts. In these embodiments, the derivatives can be in the form of multiple different salts, or some compounds of the mixture can be in the form of certain salts while other compounds are in the form of different salts, or not in a salt form. In certain embodiments, a mono ester and a di ester is administered together. In another embodiment, a mono ester, a di ester and a tri ester are administered together. In yet another embodiment, a mono, di or tri ester is administered in combination with any other andrographolide derivative. In one embodiment, the ester is a di carboxylic acid ester. In another embodiment, the ester is succiimc acid.

In another embodiment, the andrographolide derivatives described above may be useful for inhibition of a viral protease. A method is therefore provided including administering a compound described herein for the inhibition of a viral protease. The inhibition of a viral protease can be in vivo or in vitro, but in certain embodiments is in vivo administration to an infected host, for example a host infected with a virus that can be inhibited by reducing activity of a viral protease.

In separate embodiments of the invention, the andrographolide derivatives described above are useful for treatment of viral infections non-Flaviviridae viruses. Therefore in one embodiment, a method is provided including administering an andrographolide derivative as described herein to a host infected with, or at risk of infection with, a virus selected from a Retroviridae, Picornaviridae, Herpesviridae, Flaviviradae, Coronaviridae, and Togaviridae family virus. Specific viruses that may be treated with an andrographolide derivative described herein are a piconavirus, cytomegalovirus (CMV), herpes simplex virus type 1 (HSV-1), herpes simplex virus type 2 (HSV-2), a human respiratory coronavirus, alphavirus or rubivirus. As described in the background of the invention, sinbis and semliki forest virus are examples of alphaviruses, and rubella virus is a member of the rubivirus genus.

Injectable extracts of *Andrographis paniculata* that include certain esters of andrographolide have been established to be safe to humans and have been used for a variety of medicinal properties; however, prior to the present invention, it was unknown that derivatives of andrographolide are effective against Flaviviridae viruses, including hepatitis C virus. In one embodiment the efficacy of the compound is determined by measuring the reduction of viral-induced cell killing and the reduction in viral yields. In preferred embodiments the compound exhibits an $EC_{50}$ of less than 25, 15, 10, 5, or 1 micromolar.

In another embodiment, the active compound can be administered in combination or alternation with another anti-Flaviviridae agent, including an anti-flavivirus, anti-pestivirus or anti-HCV agent. In combination therapy, an effective dosage of two or more agents are administered together, whereas during alternation therapy an effective dosage of each agent is administered serially. The dosages will depend on absorption, inactivation, and excretion rates of the drug as well as other factors known to those of skill in the art.

It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Nonlimiting examples of compounds that can be used in combination with the andrographolide derivatives are lipoic acid and n-acetyl cysteine.

DEFINITIONS

The term "independently" is used herein to indicate that the variable which is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

Whenever a range is refered to herein, such as $C_1$ to $C_6$ alkyl, it is meant to refer independently to each member of the range. For example, $C_1$ to $C_6$ alkyl (or $C_{1-6}$ alkyl) means, independently, $C_1$, $C_2$, $C_3$, $C_4$, $C_5$ or $C_6$ alkyl.

The term "alkyl", alone or in combination, means an acyclic, saturated straight, branched, or cyclic, primary, secondary, or tertiary hydrocarbon, including those containing from 1 to 10 carbon atoms or from 1 to 6 carbon atoms. Said alkyl radicals may be optionally substituted with groups as defined below. The term alkyl specifically includes but is not limited to methyl, ethyl, propyl, isopropyl, cyclopropyl, butyl, isobutyl, t-butyl, sec-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl, heptyl, octyl; nonyl, decyl, trifluoromethyl and difluoromethyl. The term includes both substituted and unsubstituted alkyl groups. Moieties with which the alkyl group can be substituted include but are not limited to, for example, hydroxyl, halo, nitro, cyano, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Third Edition, 1999, hereby incorporated by reference. The term "cycloalkyl", alone or in combination, means a saturated or partially unsaturated cyclic alkyl, having from 1 to 10 carbon atoms, including but not limited to mono- or bi-cyclic ring systems such as cyclopropyl, cyclobutyl, cyclopentyl, cyclohexenyl, and cyclohexyl. The term lower alkyl, as used herein, and unless otherwise specified, refers to a $C_1$ to $C_5$ saturated straight, branched, or if appropriate, a cyclic (for example, cyclopropyl) alkyl group.

The term carbohydrate, used herein includes any of the group of organic compounds composed of carbon, hydrogen, and oxygen, including sugars, starches, and celluloses.

The term "alkenyl", alone or in combination, means an acyclic, straight, branched, or cyclic, primary, secondary, or tertiary hydrocarbon, including those containing from 2 to 10 carbon atoms or from 2 to 6 carbon atoms, wherein the substituent contains at least one carbon-carbon double bond. Said alkenyl radicals may be optionally substituted. Examples of such radicals include, but are not limited to, ethylene, methylethylene, and isopropylidene.

The term "alkynyl" refers to an unsaturated, acyclic hydrocarbon radical, linear or branched, in so much as it contains one or more triple bonds, including such radicals containing about 2 to 10 carbon atoms or having from 2 to 6 carbon atoms. The alkynyl radicals may be optionally substituted with groups as defined herein. Examples of suitable alkynyl radicals include, but are not limited to, ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "acyl", alone or in combination, means a group containing a carbonyl bonded to a radical. Radicals can include, but are not limited to, those selected from, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Non-limiting examples of "acyl" are formyl, acetyl, benzoyl, trifluoroacetyl, phthaloyl, malonyl, nicotinyl, and the like.

The terms "alkoxycarbonyl" and "carboalkoxy" are used interchangeably. Used alone or in combination, the terms refer to the radical —C(O)OR, wherein R is alkyl that can be optionally substituted as defined herein.

The term "hydroxy", alone or in combination means the radical —OH.

The term "sulfonyl", alone or in combination means the radical —$S(O)_2$—.

The term "oxo" refers to an oxygen attached by a double bond (═O).

The terms "carbocycle" and "carbocyclic", alone or in combination, means any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

The term "aryl", alone or in combination, means a carbocyclic aromatic system containing one, two or three rings wherein such rings may be attached together in a pendent manner or may be fused. Examples of aryl groups include phenyl, benzyl and biphenyl. The "aryl" group can be optionally substituted where possible, for example, with one or more of the moieties including but not limited to those selected from the group consisting of alkyl, hydroxyl, halo, nitro, cyano, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art. In addition, adjacent groups on an "aryl" ring may combine to form a 5- to 7-membered saturated or partially unsaturated carbocyclic, aryl, heteroaryl or heterocyclic ring, which in turn may be substituted as above. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenyl-methyl; 4-tertiarybutylphenyl; 4-tertiarybutylphenylmethyl and the like The term aralkyl or arylalkyl refers to an aryl group with an alkyl substituent, and, unless otherwise specified, refers to an aryl group as defined above linked to the molecule through an alkyl group as defined above. The term alkaryl or alkylaryl refers to an alkyl group with an aryl substituent, and, unless otherwise specified, refers to an alkyl group as defined above linked to the molecule through an aryl group as defined above. In each of these groups, the alkyl group can be optionally substituted as describe above and the aryl group can be optionally substituted with one or more moieties described in the definition of aryl either unprotected, or protected as necessary, as known to those skilled in the art, for example, as taught in Greene, et al., *Protective Groups in Organic Synthesis*, John Wiley and Sons, Second Edition, 1991.

The "spacer" can be any divalent moiety that does not negate the biological activity of the molecule, including, but not limited to, a polymer, oligomer, an alkyl; alkenyl; alkynyl; alkaryl; aralkyl; aryl; heteroaryl; or heterocycle divalent moiety or a divalent moiety selected from the group consisting of —(CH$_2$)$_n$—, —(CH$_2$)$_n$—CO—; —CO—(CH$_2$)$_n$—; —N—(CH$_2$)$_n$—; —CO—(CH$_2$)$_n$—; —S—(CH$_2$)$_n$—; —(O-alkyl)-; —(S-alkyl)-, —(O-alkyl)-, —P(O)$_2$R$^4$; —(O-alkyl)-; —(CHOH)$_x$(CH2)$_{y-x}$ (i.e., a polyoxalkylene); —(CH(alkyl))$_x$(CH$_2$)$_{y-x}$ or —(CHOH)$_x$(CH$_2$)$_{y-x-z}$(CH(alkyl))$_z$ wherein x+y=n, and wherein x, y, and z and can be any integer from 0, 1, 2, 3, 4, 5, 6, 7, 8, 9, 10, 11 or 12; x, y and z can be randomly dispersed among the moiety, and wherein n is 0, 1, 2, 3, 4, 5, 6, 7, 8, 9, 10, 11 or 12. The spacer can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of the compound, either unprotected, or protected as necessary, as known to those skilled in the art, for example, as taught in Greene, et al., *Protective Groups in Organic Synthesis*, John Wiley and Sons, Second Edition, 1991.

The term "protected" as used herein and unless otherwise defined refers to a group that is added to a heteroatom to prevent its further reaction or for other purposes. A wide variety of oxygen and nitrogen protecting groups are known to those skilled in the art of organic synthesis.

The term halo or halogen, as used herein, includes chloro, bromo, iodo, and fluoro.

The terms "alkoxy" and "alkoxyalkyl" embrace linear or branched oxy-containing radicals each having alkyl portions of one to about ten carbon atoms, such as methoxy radical. The term "alkoxy" is —OR, wherein R is alkyl, including cycloalkyl. The term "alkoxyalkyl" also embraces alkyl radicals having one or more alkoxy radicals attached to the alkyl radical, that is, to form monoalkoxyalkyl and dialkoxyalkyl radicals. The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present. Other alkoxy radicals are "lower alkoxy" radicals having one to six carbon atoms. Non-limiting examples of such radicals include methoxy, ethoxy, propoxy, butoxy and tert-butoxy alkyls. The "alkoxy" radicals may be further substituted with, for example, one or more halo atoms, such as fluoro, chloro or bromo, to provide "haloalkoxy" radicals. Non-limiting examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "alkylthio" and "arylthio" are —SR, wherein R is alkyl or aryl, respectively. Similarly, the term "alkylsulfinyl" is R—SO$_2$, wherein R is alkyl and the term "alkylsulfonyl" is defined as R—SO$_3$, wherein R is alkyl.

The term heteroaryl or heteroaromatic, as used herein, refers to an aromatic that includes at least one sulfur, oxygen, nitrogen or phosphorus in the aromatic ring. The heteroaromatic group can be optionally substituted as described above for aryl. The heteroaromatic can be partially or totally hydrogenated as desired. Functional oxygen and nitrogen groups on the heteroaryl group can be protected as necessary or desired. Suitable protecting groups are well known to those skilled in the art, and include, but are not limited to, trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term "heterocyclic" refers to a nonaromatic cyclic group that may be partially (contains at least one double bond) or fully saturated and wherein there is at least one heteroatom, such as oxygen, sulfur, nitrogen, or phosphorus in the ring. The heterocyclic group can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

Nonlimiting examples of heterocylics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl, aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired.

The term amino acid refers to naturally occurring and synthetic amino acids, and includes, but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, and histidinyl.

The term "ether", as used herein, refers to oxygen that is disubstitued with independent alkyl groups or two alkyl groups that together formed a ring or a bridge. Non-limiting examples include 3-(imidazol-1-yl)propoxy, 4-(imidazol-1-yl)butoxy, 5-(imidazol-1-yl)pentoxy, 2-(benzimidazol-1-yl)ethoxy, 3-(benzimidazol-1-yl)-propoxy, 4-(benzimidazol-1-yl)butoxy, 5-(benzimidazol-1-yl)pentoxy, 2-(tetrahydrobenzimidazol-1-yl)ethoxy, 3-(tetrahydrobenzimidazol-1-yl)propoxy, 4-(tetrahydrobenzimidazol-1-yl)butoxy, 5-(tetrahydrobenzimidazol-1-yl)pentoxy, ethoxy, n-propoxy, or isopropoxy. The ethers also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al, *Protective Groups in Organic Synthesis*, John Wiley and Sons, Second Edition, 1991.

The term "sulfoxy," as used herein, refers to a pentavalent sulfur moiety. Non-limiting examples include methanesulphonyloxy, ethanesulphonyloxy, n-propanesulphonyloxy, isopropanesulphonyloxy, n-butanesulphonyloxy, benzenesulphonyloxy, 4-fluorobenzenesulphonyloxy, 4-bromobenzenesulphonyloxy, 4-methylbenzenesulphonyloxy, 4-methoxybenzene-sulphonyloxy, 3,4-dichlorobenzenesulphonyloxy, phenylmethanesulphonyloxy, 2-phenylethanesulphonyloxy, or 3-phenylpropanesulphonyloxy. The sulfoxy group also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "amide", as used herein, refers to a carbonyl moiety wherein the non-alkyl moiety is formed from an amine. The amide group also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "imide," as used herein, refers to a carbonyl derivative wherein the carbonyl carbon is double bonded to a nitrogen rather than a oxygen. The imide also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "sulfamoyl" is a hexavalent sulfur covalently bound to at least two oxygens and a nitrogen. The sulfamoyl group also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "carbamide" refers to a carbonyl flanked on both sides by a nitrogen. The carbamide group also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "thio" refers to a sulfur covalently bound to a hydrogen or a carbon based group. The term "thiol", alone or in combination, means the radical —SH. Non-limiting examples include methylmercapto, ethylmercapto, n-propylmercapto, isopropylmercapto or n-butylmercapto, ethylthio, n-propylthio or isopropylthio group. The thio group also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "urethane" or "carbamate" refers to —OC(O)NR$^4$R$^5$ in which R$^4$ and are independently selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the carbamide typically comprise a phenyl group. The term "lower carbamide" refers to an carbamide group in which the noncarbonyl moiety is a lower alkyl. The carbamide group also can be optionally substituted with one or more moieties, including, but not limited to, those selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "host", as used herein, refers to a unicellular or multicellular organism in which the virus can replicate, including cell lines and animals, and preferably a human. Alternatively, the host can be carrying a part of the HCV, flavivirus or pestivirus genome, whose replication or function can be altered by the compounds of the present invention. In certain embodiments, the term host specifically refers to infected cells, cells transfected with all or part a viral genome, such as a genome from a flavivirus, pestivirus or HCV, and animals, in particular, primates (including chimpanzees) and humans. In most animal applications of the present invention, the host is a human patient. Veterinary applications, in certain indications, however, are anticipated by the present invention.

Pharmaceutically Acceptable Salts, Esters and Prodrugs

In cases where compounds are sufficiently basic or acidic to form stable nontoxic acid or base salts, administration of the compound as a pharmaceutically acceptable salt may be appropriate. Pharmaceutically acceptable salts or complexes refers to salts or complexes of the described compounds that retain the desired biological activity of the parent compound and exhibit minimal, if any, undesired toxicological effects. Pharmaceutically acceptable salts include, but are not limited to, those derived from pharmaceutically acceptable inorganic or organic bases and acids, from alkali metals such as potassium and sodium and alkaline earth metals such as calcium and magnesium. Pharmaceutically acceptable salts may be obtained, for example, by reacting a sufficiently basic compound such as an amine with a suitable acid affording a physiologically acceptable anion.

Nonlimiting examples of suitable salts are (a) acid addition salts formed with inorganic acids (for example, hydrochloric acid, hydrobromic acid, sulfuric acid, phosphoric acid, nitric acid, carbonic acid, bicarbonic acid, and the like), and salts formed with organic acids such as acetic acid, citric acid, malonic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, tosylic acid, methanesulfonic acid, α-ketoglutaratic acid, α-glycerophosphoric acid, polygalacturonic acid, and the like; (b) base addition salts formed with polyvalent metal cations such as sodium, potassium, lithium, zinc, calcium, bismuth, barium, magnesium, aluminum, copper, cobalt, nickel, cadmium, and the like, or with an organic cation formed from N,N-dibenzylethylenediamine, ammonium, or ethylenediamine; or (c) combinations of (a) and (b); e.g., a zinc tannate salt or the like.

The active compound can be a diester or monoester of andrographolide. The term "ester" refers to a carbonyl flanked by an alkoxy group and a carbon based group. The ester(s) of andrographolide is(are) formed from one or more dicarboxylic acids including, but not limited to, oleic, malonic, succinic acid, glutaric acid, adipic acid, suberic acid, sebacic acid, azelaic acid, maleic, fumaric, phthalic, isophthalic, pimelic acid, acetylenedicarboxylic acid, glutaconate acid, dihydromuconic acid, dodecanedionic acid, isocinchomeronic acid, cinchomeronic acid, glutidinic acid, dinicotinic acid, dipicolinic acid, 2,3-pyridinedicarboxylic acid, 5-ethyl-2,3-pyridinedicarboxylic acid, pyrazine-2,3-dicarboxylic acid, pyrazine-2,5-dicarboxylic acid, pyrazine-2,6-dicarboxylic acid, furan-2,5-dicarboxylic acid, 2-oxotetrahydrofuran-4,5-dicarboxylic acid, 6-oxo-1,4,5,6-tetrahydropyridazin-3-carboxylic acid, trans-cyclohexane-1,3-dicarboxylic acid, dimethyl ester, 4,4'-stilbenedicarboxylic acid, azodicarboxylic acid, pyrazole-3,4-dicarboxylic acid, 1,4-cyclohexanedicarboxylie acid, cyclohexane-1,1-dicarboxylic acid, naphthalene-2,6-dicarboxylic acid, 2,4,6-trimethyl-3,5-pyridinedicarboxylic acid, chlorendic acid, 3-tert-butyl adipic acid, 2-tert-butyl adipic acid, acetyl-butanedioic acid, (dimethoxyphosphinothioyl)thio-butanedioic acid, 3,4-(dimethoxyphenyl)methylene-propanedioic acid, (dimethoxyphosphinyl) thiobutanedioic acid, (2z,4z)-2,5-dimethyl-2,4-hexadienedioic acid, trimethylbutanedioic acid, triethylbutanedioic acid, phenylmalonic acid, 2,2,6,6-tetramethylpimelic acid, (tetrapropenyl)-butanedioic acid, 1,4-diisodecylsulfobutanedioic acid, 3-methylhexanedioic acid, 2-methylhexanedioic acid, (2s,4r)-4-methylglutamic acid, diethylbutanedioic acid, dibutylbutanedioic acid, dipentylbutanedioic acid, dihexylbutanedioic acid, diheptylbutanedioic acid, dioctylbutanedioic acid, 3,3-dimethylglutaric acid, 1,3-dithiolan-2-ylidenepropanedioie acid, 4-hydroxy benzylidene malonic acid, di-1,4-o-benzoyl-tartaric acid, di-1,4-o-toluoyl-tartaric acid, diacetyl-tartaric acid, iminoeliacteic acid, threonic acid, 4,5-imidazoledicarboxylic acid, pyrazole-3,4-dicarboxylic acid, 3,5-pyrazoledicarboxylie acid, 2-bromo-malonic acid, 2-iodo-malonic acid, 2-fluoro-malonic acid, 2-chloro-malonic acid, cyclopropane-1,1-dicarboxylic acid, cyclobutane-1,1-dicarboxylic acid, cyclopentane-1,1-dicarboxylic acid, cycloheaxne-1,1-dicarboxylic acid, cycloheptane-1,1-dicarboxylic acid, cyclooctane-1,1-dicarboxylic acid, citramalate, itaconic acid, mesaconic acid, oxalic acid, dibromomaleic acid, dichloromaleic acid, diiodomaleic acid, difluoromaleic acid, diazidomaleic acid, dicyanoaleic acid, diaminomaleic acid, tetrafluorosuccinic acid, tetraiodosuccinic acid, tetrachlorosuccinic acid, tetrabromosuccinic acid, dichlorodibromosuccinic acid, dichlorodiiodosuccinic acid, dichlorodifluorosuccinic acid, dibromodiiodosuccinic acid, dichlorodifluorosuccinic acid, difluorodiiodosuccinic acid, dibromodifluorosuccinic acid, methylmalonic acid, ethylmalonic acid, butylmalonic acid, pentylmalonic acid, hexylmalonic acid, heptylmalonic acid, octylmalonic acid, triazoledicaboxylic acid, thiomalic acid, dithiomalic acid, trimalic acid, diglycolic acid, acetone dicarboxylic acid, ketoglutaric acid, dimethyl nitomalonic acid, citramalonic acid, n-(phosphonomethyl)-iminodiacetic acid, octafluoroadipic acid, octaiodoadipic acid, octabromoadipic acid, octachlorodipic acid, 4,5-isoxazoledicarboxylic acid, diethyl azodicarboxylic acid, tidiacic, 4,5-imidazoledicarboxylic acid, azoxybenzene-4,4'-dicarboxylic acid, diazodicarboxylic acid, citric acid, (trifluoroacetamido)succinic acid, 3,4-dimethylthieno(2,3-b)thiophene-2,5-dicarboxylic acid, acetoxysuccinic acid, acetinic acid, isocitric acid, hydromuconic acid, oxoadipic acid, tricarballylic acid, nitrilotriacetic acid, n-acetyl aspartic acid or terephthalic acid esters or their pharmaceutically acceptable salts, including sodium or potassium salts. In an alternative embodiment, one of the dicarboxylic acid esters is linked to two hydroxyl groups of the andrographolide to form an internal ringed structure. In another embodiment, a mono- or di-succinic acid ester of andrographolide, and particularly a disuccinic acid ester wherein one of the esters is internally cyclized to the andrographolide ring, is administered.

In another embodiment, the andrographolide is in the form of a pharmaceutically acceptable ester to, for example, increase the water solubility of the compound over the parent andrographolide and that exhibits HCV activity. Such pharmaceutically acceptable esters include, but are not limited to, saturated and unsaturated dicarboxylic acids and salts thereof, amino carboxylic acids and salts thereof, aldehyde containing carboxylic acids and salts thereof, an amine group, a salt of an amine group, an amide group, aldehydes groups and the salts thereof. In yet another embodiment, the ester has a functional moiety selected from the group consisting of sulfonic acids, sulfonic acid esters, phosphoric acids, phosphoric acid esters, cyclic phosphates, polyhydroxyalkyl groups, carbohydrate group, $C(O)$-spacer-$SO_3H$, wherein spacer is —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S)$—, -(aryl-O)—, —(O-aryl)-, -(alkyl-O)—, —(O-alkyl)-; n is 0, 1, 2, 3, 4, 5, 6, 7, 8, 9, or 10; $C(O)$-spacer-$SO_3M$, wherein M is a metal used to form a pharmaceutically acceptable salt, for example, sodium or potassium, $C(O)$-spacer-$PO_3H_2$, $C(O)$-spacer-$PO_3M_2$, $C(O)$-spacer-$PO_3HM$, $C(O)$-spacer-$PO_4H$, $C(O)$-spacer-$PO_4M$, $SO_3M$, —$PO_3H_2$—$PO_3M_2$, —$PO_3HM$, cyclic phosphates, polyhydroxyalkyl, carbohydrate groups, $C(O)$-spacer-$[O(C_{1-3}\ alkyl)_p]_n$, wherein n is as defined above and p is 1, 2, or 3, —$[O(C_{1-3}\ alkyl)_p]_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

Pharmaceutically acceptable prodrugs refer to a compound that is metabolized, for example, hydrolyzed (as in the case of pharmaceutically acceptable esters) or oxidized, in the host to form the compound of the present invention. Prodrug design is discussed generally in Hardma et al. (Eds.), *Goodman and Gilman's The Pharmacological Basis of Therapeutics,* 9th ed., pp. 11-16 (1996). A thorough discussion is also provided by Higuchi, et al., in *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). Typically, administration of a drug is followed by elimination from the body or some biotransformation whereby the biological activity of the drug is reduced or eliminated. Alternatively, a biotransformation process can lead to a metabolic by-product that is more or equally active compared to the drug initially administered. Prodrugs, therefore, encompass compounds that are converted by some means to pharmacologically active metabolites. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, an amino acid, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against flavivirus, pestivirus or HCV, or are metabolized to a compound that exhibits such activity.

Combination and/or Alternation Therapy

It has been recognized that drug-resistant variants of viruses, including HCV, can emerge after prolonged treatment with an antiviral agent. Drug resistance most typically occurs by mutation of a gene that encodes for an enzyme used in viral replication. Additionally, some HCV genotypes possess an interferon-sensitivity determining region that imparts interferon resistance. The efficacy of a drug against viral infection, including inhibition of viral proteases, can be prolonged, augmented, or restored by administering the compound in combination or alternation with a second, and perhaps third, antiviral compound that induces a different mutation from that caused by the principle drug. Because a resistance gene may already exist, combination therapy may allow one to target different sets of viral genes necessary for replication. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification.

For example, the compounds can be administered in combination or alternation with an interferon based therapy (see, for example, Battaglia, A. M. et al., *Ann. Pharmacother.* 34:487-494, 2000); Berenguer, M. et al. *Antivir. Ther.* 3(Suppl. 3):125-136, 1998). In addition, a number of patents disclose treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696.

Idenix Pharmaceuticals, Ltd. discloses branched nucleosides, and their use in the treatment of HCV and flaviviruses and pestiviruses in U.S. Pat. Nos. 6,812,219, 6,914,054, US Patent Publication No. 2003/0050229 A1 and US Patent Publication No. 2003/0060400 A1, which correspond to International Publication Nos. WO 01/90121 and WO 01/92282. A method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or prodrug thereof, administered either alone or in combination, optionally in a pharmaceutically acceptable carrier. See also U.S. Patent Publication Nos. 2004/0006002 and 2004/0006007 as well as WO 03/026589 and WO 03/026675. Idenix Pharmaceuticals, Ltd. also discloses in US Patent Publication No. 2004/0077587 pharmaceutically acceptable branched nucleoside prodrugs, and their use in the treatment of HCV and flaviviruses and pestiviruses in prodrugs. See also PCT Publication Nos. WO 04/002422, WO 04/002999, and WO 04/003000.

Biota Inc. discloses various phosphate derivatives of nucleosides, including 1', 2', 3' or 4'-branched β-D or β-L nucleosides, for the treatment of hepatitis C infection in International Patent Publication WO 03/072757 and U.S. Publication No. 2004/0059104.

Emory University and the University of Georgia Research Foundation, Inc. (UGARF) discloses the use of 2'-fluoronucleosides for the treatment of HCV in U.S. Pat. No. 6,348,587. See also U.S. Pat. No. 6,911,424 and International Patent Publication WO 99/43691.

BioChem Pharma Inc. (now Shire Biochem, Inc.) discloses the use of various 1,3-dioxolane nucleosides for the treatment of a Flaviviridae infection in U.S. Pat. No. 6,566,365. See also U.S. Pat. Nos. 6,340,690 and 6,605,614; US Patent Publication Nos. 2002/0099072 and 2003/0225037, as well as International Publication No. WO 01/32153 and WO 00/50424.

BioChem Pharma Inc. (now Shire Biochem, Inc.) also discloses various other 2'-halo, 2'-hydroxy and 2'-alkoxy nucleosides for the treatment of a Flaviviridae infection in US Patent Publication No. 2002/0019363 as well as International Publication No. WO 01/60315 (PCT/CA01/00197; filed Feb. 19, 2001).

U.S. Pat. No. 6,660,721; US Patent Publication Nos. 2003/083307 A1, 2003/008841 A1, and 2004/0110718; as well as International Patent Publication Nos. WO 02/18404; WO 02/100415, WO 02/094289, and WO 04/043159; filed by F. Hoffmann-La Roche A G, discloses various nucleoside analogs for the treatment of HCV RNA replication.

ICN Pharmaceuticals, Inc. discloses various nucleoside analogs that are useful in modulating immune response in U.S. Pat. Nos. 6,495,677 and 6,573,248. See also WO 98/16184, WO 01/68663, and WO 02/03997 and U.S. Publication No. 2002-0095033.

Pharmasset Limited discloses various nucleosides and antimetabolites for the treatment of a variety of viruses, including Flaviviridae, and in particular HCV, in US Patent Publication Nos. 2003/0087873, 2004/0067877, 2004/0082574, 2004/0067877, 2004/002479, 2003/0225029, 2004/0002476 and 2002/00555483, as well as International Patent Publication Nos. WO 02/32920, WO 01/79246, WO 02/48165, WO 03/068162, WO 03/068164, WO 04/009020 and WO 04/013298.

Merck & Co., Inc. and Isis Pharmaceuticals disclose in U.S. Pat. No. 6,777,395, US Patent Publication No. 2002/0147160, 2004/0072788, 2004/0067901, and 2004/0110717; as well as the corresponding International Patent Publication Nos. WO 02/057425 (PCT/US02/01531) and WO 02/057287 (PCT/US02/03086) various nucleosides, and in particular several pyrrolopyrimidine nucleosides, for the treatment of viruses whose replication is dependent upon RNA-dependent RNA polymerase, including Flaviviridae, and in particular HCV. See also WO 2004/000858, WO 2004/003138, WO 2004/007512, and WO 2004/009020.

US Patent Publication No. 2003/028013 and 2004/0023921 as well as International Patent Publication Nos. WO 03/051899, WO 03/061576, WO 03/062255 WO 03/062256, WO 03/062257, and WO 03/061385, filed by Ribapharm, also are directed to the use of certain nucleoside analogs to treat hepatitis C virus.

Genelabs Technologies disclose in US Patent Publication No. 2004/0063658 as well as International Patent Publication Nos. WO 03/093290 and WO 04/028481 and U.S. Publications 2004/0147464 and 2005/0119200, various base modified derivatives of nucleosides, including 1', 2', 3' or 4'-branched β-D or β-L nucleosides, for the treatment of hepatitis C infection.

Other compounds currently in clinical development for treatment of hepatitis C virus include, for example: Interleukin-10 by Schering-Plough, IP-501 by Interneuron, Merimebodib VX-497 by Vertex, AMANTADINE (Symmetrel) by Endo Labs Solvay, HEPTAZYME by RPI, IDN-6556 by Idun Pharma., XTL-002 by XTL, HCV/MF59 by Chiron, CIVACIR by NABI, LEVOVIRIN by ICN, VIRAMIDINE by ICN, ZADAXIN (thymosin alfa-1) by Sci Clone, CEPLENE (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc. and JTK 003 by AKROS Pharma.

Several patents disclose protease inhibitors for the treatment of HCV. For example, U.S. Pat. No. 6,004,933 to Spruce et al. discloses a class of cysteine protease inhibitors for inhibiting HCV. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. Other substrate-based NS3 protease inhibitors have been previously described (see, for example, Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (see, for example, Llinas-Brunet et al, Hepatitis C inhibitor peptide analogues, PCT WO 99/07734). Selective NS3 inhibitors, also include, for example, those based on the macromolecule elgin c, isolated from leech (see, for example, Qasim M. A. et al., *Biochemistry*, 1997, 36, 1598-1607);

U.S. Pat. No. 5,972,347 to Eder et al. and U.S. Pat. No. 5,969,109 to Bona et al. disclose a vaccine for treating HCV. U.S. Pat. No. 6,030,960 to Morris-Natschke et al. discloses the use of certain alkyl lipids to inhibit the production of hepatitis-induced antigens, including those produced by the HCV virus.

U.S. Pat. No. 5,858,389 to Elsherbi et al. discloses the use of squalene for treating hepatitis C.

U.S. Pat. No. 5,849,800 to Smith et al. discloses the use of amantadine for treatment of Hepatitis C.

U.S. Pat. No. 5,491,135 to Blough et al. discloses the use of N-(phosphonoacetyl)-L-aspartic acid to treat flaviviruses such as HCV.

U.S. Pat. No. 6,027,729 discloses and claims polypeptides encoded by the HCV genome. U.S. Pat. No. 5,922,857 to Han et al. disclose nucleic acids corresponding to the sequence of the pestivirus homology box IV area for controlling the translation of HCV. The use of ribozymes to treat HCV is disclosed in U.S. Pat. No. 6,043,077 to Barber et al., and U.S. Pat. Nos. 5,869,253 and 5,610,054 to Draper et al. PCT application WO 99/29350 discloses compositions and methods of treatment for hepatitis C infection comprising the administration of antisense oligonucleotides which are complementary and hybridizable to HCV-RNA. Similarly, U.S. Pat. No. 6,001,990 discloses antisense oligonucleotides and methods of using these antisense oligonucleotides for inhibiting HCV-RNA translation.

U.S. Pat. No. 5,128,458 discloses β-D-2',3'-dideoxy-4'-thioribonucleosides as antiviral agents. U.S. Pat. No. 5,446,029 discloses that 2',3'-dideoxy-3'-fluoronucleosides have anti-hepatitis activity.

Additional compounds have been described for the treatment of Flaviviridae infection. For example, U.S. Pat. No. 5,891,874 discloses a series of benzimidazole compounds and a method for inhibiting Flaviviridae including hepatitis C virus using such compounds. U.S. Pat. No. 6,001,799 discloses a method of treating hepatitis C in non-responders to interferon comprising administering at least one thymosin.

Other compounds include non-substrate-based inhibitors such as 2,4,6-trihydroxy-3-nitro-benzamide derivatives (see, for example, Sudo K. et al., *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group;

Thiazolidine derivatives have been identified, for example, that show relevant inhibition in a reverse-phase HPLC assay with an NS3/4A fusion protein and NS5A/5B substrate (see, for example, Sudo K. et al., *Antiviral Research*, 1996, 32, 9-18), especially compound RD-1-6250, possessing a fused cinnamoyl moiety substituted with a long alkyl chain, RD4 6205 and RD4 6193.

Additional thiazolidines and benzanilides, for example, are identified in Kakiuchi N. et al. *J. EBS Letters* 421, 217-220; Takeshita N. et al. *Analytical Biochemistry*, 1997, 247, 242-246.

Phenanthrenequinone have been described possessing activity against protease in a SDS-PAGE and autoradiography assay, for example, isolated from the fermentation culture broth of *Streptomyces* sp., Sch 68631 (see, for example, Chu M. et al., *Tetrahedron Letters*, 1996, 37, 7229-7232), and Sch 351633, isolated from the fungus *Penicillium griseofulvum*, which demonstrates activity in a scintillation proximity assay (see, for example, Chu M. et al., *Bioorganic and Medicinal Chemistry Letters* 9, 1949-1952);

Helicase inhibitors have been described (see, for example, Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554). Inhibitors of IRES-dependent translation have also been described (see, for example, Ikeda N et al., Agent for the prevention and treatment of hepatitis C, Japanese Patent Pub. JP-08268890; Kai Y. et al. Prevention and treatment of viral diseases, Japanese Patent Pub. JP-10101591).

Polymerase inhibitors that have been described as potentially useful for treatment of a viral infection include: nucleotide analogues, for example, gliotoxin (see, for example, Ferrari R. et al. *Journal of Virology*, 1999, 73, 1649-1654); the natural product cerulenin (see, for example, Lohmann V. et al., *Virology*, 1998, 249, 108-118); and non-nucleoside polymerase inhibitors, including, for example, compound R803 (see, for example, WO 04/018463 A2 and WO 03/040112 A1, both to Rigel Pharmaceuticals, Inc.); substituted diamine pyrimidines (see, for example, WO 03/063794 A2 to Rigel Pharmaceuticals, Inc.); benzimidazole derivatives (see, for example, *Bioorg. Med. Chem. Lett.*, 2004, 14:119-124 and *Bioorg. Med. Chem. Lett.*, 2004, 14:967-971, both to Boehringer Ingelheim Corporation); N,N-disubstituted phenylalanines (see, for example, *J. Biol. Chem.*, 2003, 278:9495-98 and *J. Med. Chem.*, 2003, 13:1283-85, both to Shire Biochem, Inc.); substituted thiophene-2-carboxylic acids (see, for example, *Bioorg. Med. Chem. Lett.*, 2004, 14:793-796 and

*Bioorg. Med. Chem. Lett.,* 2004, 14:797-800, both to Shire Biochem, Inc.); α,γ-diketoacids (see, for example, *J. Med. Chem.,* 2004, 14-17 and WO 00/006529 A1, both to Merck & Co., Inc.); and meconic acid derivatives (see, for example, *Bioorg. Med. Chem. Lett.,* 2004, 3257-3261, WO 02/006246 A1 and WO03/062211 A1, all to IRBM Merck & Co., Inc.).

Antisense phosphorothioate oligodeoxynucleotides (S-ODN) complementary, for example, to sequence stretches in the 5' non-coding region (NCR) of the virus have been described (see, for example, Alt M. et al., *Hepatology,* 1995, 22, 707-717), or to nucleotides 326-348 comprising the 3' end of the NCR and nucleotides 371-388 located in the core coding region of the HCV RNA (see, for example, Alt M. et al., *Archives of Virology,* 1997, 142, 589-599; Galderisi U. et al., *Journal of Cellular Physiology,* 1999, 181, 251-257).

Additional compounds include nuclease-resistant ribozymes (see, for example, Maccjak, D. J. et al., *Hepatology* 1999, 30, abstract 995).

Other examples of nucleoside analogs that have been developed for the treatment of Flaviviridae infections include lipoic acid or n-acetyl cysteine or a prodrug or pharmaceutically acceptable salt thereof.

Other miscellaneous compounds including 1-amino-alkylcyclohexanes (for example, U.S. Pat. No. 6,034,134 to Gold et al.), alkyl lipids (for example, U.S. Pat. No. 5,922,757 to Chojkier et al.), vitamin E and other antioxidants (for example, U.S. Pat. No. 5,922,757 to Chojkier et al.), squalene, amantadine, bile acids (for example, U.S. Pat. No. 5,846,964 to Ozeki et al.), N-(phosphonoacetyl)-L-aspartic acid (for example, U.S. Pat. No. 5,830,905 to Diana et al.), benzenedicarboxamides (for example, U.S. Pat. No. 5,633,388 to Diana et al.), polyadenylic acid derivatives (for example, U.S. Pat. No. 5,496,546 to Wang et al.), 2',3'-dideoxyinosine (for example, U.S. Pat. No. 5,026,687 to Yarchoan et al.), and benzimidazoles (for example, U.S. Pat. No. 5,891,874 to Colacino et al.).

Pharmaceutical Compositions

The described derivative of andrographolide can be formulated as pharmaceutical compositions and administered to a host infected with a Flaviviridae virus, including HCV, including a human, in any of a variety of forms adapted to the chosen route of administration, including systemically, such as orally, or parenterally, by intravenous, intramuscular, topical, transdermal or subcutaneous routes.

The derivative of andrographolide (or prodrug thereof) is included in the pharmaceutically acceptable carrier or diluent in an amount sufficient to deliver to a patient a therapeutically effective amount of compound to reduce Flaviviridae viral infection or the symptoms thereof in vivo without causing serious toxic effects in the patient treated.

A preferred dose of the derivatives of andrographolide for all of the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the prodrug can be calculated based on the weight of the parent derivative to be delivered.

The derivatives of andrographolide are conveniently administered in units of any suitable dosage form, including but not limited to one containing 7 to 3000 mg, preferably 70 to 1400 mg of active ingredient per unit dosage form. An oral dosage of 50-1000 mg is usually convenient, and more typically, 50-500 mg.

Ideally the derivatives of andrographolide should be administered to achieve peak plasma concentrations of the active compound of from about 0.2 to 70 µM, preferably about 1.0 to 10 µM. This may be achieved, for example, by the intravenous injection of an appropriate concentration of the active ingredient, optionally in saline, or administered as a bolus of the active ingredient.

The concentration of the derivative of andrographolide in the drug composition will depend on absorption, inactivation, and excretion rates of the extract as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The derivative of andrographolide may be administered at once, or may be divided into a number of smaller doses to be administered at varying intervals of time.

A preferred mode of administration of the derivative of andrographolide is oral. Oral compositions will generally include an inert diluent or an edible earner. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The derivative of andrographolide can be administered as a component of an elixir, suspension, syrup, wafer, chewing gum or the like. A syrup may contain, in addition to the active compounds, sucrose as a sweetening agent and certain preservatives, dyes and colorings and flavors. The derivatives of andrographolide can also be mixed with other active materials that do not impair the desired action, or with materials that supplement the desired action, such as antibiotics, antifungals, anti-inflammatories, or other anti-virals, including nucleoside anti-HIV compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In another embodiment, the derivatives of andrographolide are prepared with carriers that will protect the derivatives against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Modifications of the active compound can affect the bioavailability and rate of metabolism of the active species, thus providing control over the delivery of the active species. Further, the modifications can affect the antiviral activity of the compound, in some cases increasing the activity over the parent compound. This can easily be assessed by preparing the derivative and testing its antiviral activity according to the methods described herein, or other method known to those skilled in the art.

EXAMPLES

Biological Activity

Compounds can be screened for their ability to inhibit flavivirus, pestivirus, or HCV activity or to inhibit viral proteases, in vitro according to published screening methods. In one embodiment the efficacy of the antiviral compound is determined by measuring the reduction of viral-induced cell killing and the reduction in viral yields. In one embodiment, the effective concentration is from approximately 5 µM to 105 µM. In preferred embodiments the compound exhibits an $EC_{50}$ of less than 15 or 10 micromolar. In another embodiment the efficacy of the protease inhibitor can be determined by measuring the inhibition of viral proteases and the reduction of viral yields. Alternatively, the compounds can be tested using to published animal models.

Throughout the examples, compound 1, 1a or MTI-1 is interferon; compound 2, 2b or MTI-2 is ribavirin; compound 3, 3c or MTI-3 is an injectable form of an andrographolide derivative contained in an *Andrographis paniculata* extract (from Chuan-Hu-Ning; Yi-Bin Pharmaceuticals, Wuliangye Co. Ltd., Yibin, Sichaun, PR China), a mixture of succinic acid esters of andrographolide, including potassium salts thereof, supplied as a 20 mg/ml solution; and compound 4, 4d or MTI-4 is an aqueous vehicle control.

Example 1

Human Bone Marrow Cytotoxicity Assay

Bone marrow toxicity is a principal dose-limiting toxicity associated with a number of antiviral drugs (Sommadossi J P and Carlisle R *Antimicrob Agents Chemother* 31: 452-454, 1987; Sommadossi, et al. *Biochem. Pharmacol.* 44:1921-1925, 1992). Colony-forming assays for bone marrow progenitors serve as key in vitro model systems for assessing potential in vivo response to chemotherapeutic agents (Sommadossi J P and Carlisle R *Antimicrob Agents Chemother* 31: 452-454, 1987; Sommadossi, et al. *Biochem. Pharmacol.* 44:1921-1925, 1992). Therefore, candidate antiviral compounds are typically evaluated in vitro for their hematopoietic toxicity potential.

Primary human bone marrow mononuclear cells were obtained from Cambrex Bioscience (Walkersville, Md.). CFU-GM assays were performed using a bilayer soft agar in the presence of 50 units/mL human recombinant granulocyte/macrophage colony-stimulating factor, while BFU-E assays used a methylcellulose matrix containing 1 unit/mL erythropoietin (Sommadossi J P and Carlisle R *Antimicrob Agents Chemother* 31: 452-454, 1987). Cells were incubated in the presence of the compound for 14-18 days at 37° C. with 5% $CO_2$, and colonies of greater than 50 cells were counted using an inverted microscope to determine $IC_{50}$ (Sommadossi, et al. *Biochem. Pharmacol.* 44:1921-1925, 1992). Each experiment was performed in duplicate in cells from three different donors. 3'-Azido-3'-deoxythymidine (AZT) was used as a positive control.

Example 2

BVDV Assays

Isolation of Active Components

Reverse phase high performance liquid chromatography (HPLC) and gel permeation HPLC were used to purify the andrographolide derivatives. The derivatives were prefiltered through a C18 Sep-Pak column and eluted in methanol. This product was further purified by reverse phase HPLC. Samples were monitored by $UV_{254nm}$ and several peak fractions were collected and analyzed for bio-activity. A peak fraction of the extract exhibiting bio-activity was further purified by Gel-permeation HPLC having a molecular weight of approximately 532 to 570.

Antiviral Activity of Andrographolide Derivates Against a Cytopathogenic Isolate of BVDV.

Derivatives of andrographolide were tested in an in vitro assay which measures the antiviral potential against a cytopathogenic isolate of BVDV in a permissive bovine uterine cell line.

Immortalized bovine uterine cell lines have been generated that are permissive for BVDV infection and replication demonstrated by observing cytopathogenic effects, determining the expression of nonstructural proteins, and by measuring increases in viral titer after inoculation. Antiviral compounds have been evaluated in the BVDV tissue culture model including ribavirin and interferon-alpha that currently are used for the therapeutic treatment of chronic flavivirus or pestivirus infections in humans (Houghton, M., Hepatitis viruses, In: Fields Virology, Editors: Fields, B. N., Knipe, D. M., and Howley, P. M., Lippincott-Raven Publishers, Philadelphia, Pa., Chapter 32, 1035-1058, 1996). The capacity to measure the effectiveness of compounds to reduce BVDV replication in vitro provides a system for preclinical assessment of potential drugs for treatment of viral infection and for analyzing possible mechanisms of action.

Cell Lines.

A bovine uterine cell line designated NCL was generated by immortalizing primary bovine uterine cells with the SV40 large T antigen oncogene (pSV3neo; ATCC cat. #37150)

using previously described procedures (Jacob, J. R., et al., *Experimental Cell Research*, 212, 42-48 (1994); Dobrinski, I., et al., *Theriogenology*, 52(5), 875-885 (1999). The NCL cell line was shown to be permissive for BVDV infection and replication by observation of cytopathogenic effects, detection of nonstructural protein expression, and by measuring increase in viral titers following inoculation. Cell lines were maintained in MEM-E medium (Life Technologies, Grand Island, N.Y.) containing 10% bovine serum (Atlantic Biologics, Norcross, Ga.) that was gamma irradiated, negative for BVDV contamination and tested negative for antibody against BVDV, supplemented with 10 mM HEPES, gentimicin (50 μg/ml), streptomycin, and penicillin (Life Technologies). Cell lines were incubated in a humid atmosphere of 5% $CO_2$ at 37° C. Cells were passaged by dissociation of the monolayer with a solution of trypsin-EDTA (Life Technologies), diluted in culture medium, and split 1:5 to new culture flasks.

BVDV Viral Isolates.

Several isolates of BVDV have been characterized by the Diagnostic Laboratory, College of Veterinary Medicine, Cornell University (Ridpath, J. R., et al., *Virology*, 205, 66-74 (1994). The isolates lead either to a cytopath (cp) or non-cytopath (ncp) infection of permissive cells (Meyers, G. and Thiel, H.-J., *Advances in Virus Research*, 47, 53-118 (1996). The cpBVDV isolate designated NADL (ATCC #VR-534) was used in this assay. Viral stock was produced by freeze-thaw of a 75 $cm^2$ flask of NCL cells 3 days after inoculation with cpBVDV.

Methylene Blue Assay.

A method to measure visible cell numbers involved staining with methylene blue (Sigma, St. Louis, Mo.) and reading the absorbance of the stain in solution after elution from the cells. Briefly, 3 days after infection of cells with BVDV, cultures were rinsed with phosphate-buffered saline (PBS; Life Technologies) followed by fixation in a Hanks balanced salt solution (HBSS; Life Technologies) containing 1.25% glutaraldehyde (Fisher Scientific, Fair Lawn, N.J.) and 0.06% methylene blue (Sigma), for 1 hour at 37° C. The methylene blue staining solution was removed from the cultures and the culture plates were rinsed in several volumes of $H^2O$. The culture plates were allowed to air dry; this was followed by elution of the methylene blue stain from the fixed cells by incubation at controlled room temperature in a solution of PBS/50% ethanol and 1% acetic acid for 1 hour, with agitation. The absorbance of the methylene blue dye in solution was measured by an ELISA plate reader (Model EL311; Bio-Tek Instruments, Inc., Winooski, Vt.) at 630 nm. In all experiments described, calculation of cell numbers for each experimental data point was expressed as the average of three wells per experimental treatment (dilution, titer, or antiviral concentration).

Antivirals.

Ribavirin and interferon alpha (IFN-α) were used as prototype compounds establishing parameters for antiviral potential in this assay. Ribavirin (Virazole®, Viratek, Inc., Covina, Calif.) was dissolved in $H^2O$ to yield a stock concentration of 100 mM and serially diluted in culture medium prior to testing over a range of 0.049-100 μM and evaluated for cytotoxicity and antiviral effects in the NCL cell line. In previous experiments, the $EC_{90}$ was 5.83 μM, the $CC_{50}$ was 5.13 μM, and the SI 0.88.

MTI-3, an injectable form of an andrographolide derivative contained in an *Andrographis paniculata* extract (Chuan-Hu-Ning; Yi-Bin Pharmaceuticals, Wuliangye Co. Ltd., Yibin, Sichaun, PR China), thought to be a mixture of succinic acid esters of andrographolide, including potassium salts thereof, supplied as a 20 mg/ml solution was serially diluted two-fold in culture medium prior to testing over a range of 0.001-2 mg/ml and evaluated for cytotoxicity and antiviral effects in the NCL cell line.

Antiviral Assay.

The NCL cell line was grown to confluence and passaged to 96 well microtiter plates (Microtest™ 96; Becton Dickinson Labware, Franklin Lakes, N.J.), at a density of $2\times10^4$ cells/well (0.34 $cm^2$) and incubated for 1 hour to allow cell attachment. After attachment, the cells of one-half of each microtiter plate were inoculated with a cpBVDV stock diluted to yield a multiplicity of infection (m.o.i.) of 0.01 $TCID_{50}$ and incubated for 3-6 hours to allow viral attachment and penetration. Following this incubation period, the inoculum was removed and replaced with fresh growth medium.

Three quarters of both cpBVDV infected and uninfected cells were grown in the presence of antiviral compound. The remaining quarter of the microassay plate served as positive (cpVDV infected) and negative (uninfected) control wells. The medium was changed daily and cell killing was measured by the methylene blue assay 3 days post-infection with BVDV.

The culture medium was collected on day 3 post-infection and the reduction in viral yield after antiviral treatment was determined. Supernatant collected from experimental wells was serially diluted ten-fold and used to infect newly prepared NCL cells. the end-point titer, the last dilution at which complete cell killing was evident, was determined in a similar 96 well format using the methylene blue assay for cell killing 5 days after infection.

The assay allows determination of 1) the effective concentration of a compound to inhibit cell killing caused by cpBVDV by 50% ($_{ck}EC_{50}$), 2) the effective concentration to reduce the release of progeny viral yield by 90% ($_tEC_{90}$), and 3) the cytotoxic concentration of the compound by 50% ($CC_{50}$) toward normal uninfected cells.

Statistics.

Cell killing due either to viral infection or to drug cytotoxicity was calculated for each experimental data point and plotted. Regression analysis (curve fitting) was performed with SigmaPlot4.0 (Jandel Sci, San Rafael, Calif.) using the Regression Wizard library of equations which best fit the collected data.

Example 2A

Ribavirin.

Ribavirin was the prototype compound tested in this cell culture assay and served as a positive control compound.

The experimental data were from two independent assays. Cell killing was normalized to 100% of the control wells to allow comparison between experiments. Antiviral effect, cytotoxicity, and reduction in viral yield by ribavirin in each assay are shown graphically in FIG. 1. In this assay, ribavirin did not exhibit an effective concentration that inhibited greater than 50% of viral-induced cell killing ($EC_{50}$). For regression analysis, a peak, log normal, 4 parameter equation was employed to calculate the maximal effective antiviral concentration ($EC_{Ribavirin}$) against cell killing. A sigmoid, logistic, 4 parameter equation was employed to calculate a cytotoxic concentration ($CC_{50}$; drug concentration that killed 50% of uninfected NCL cells) and an effective concentration that reduced viral yield ($EC_{90}$; drug concentration that reduced viral titer by 90%). These values are provided in Table 1. The selectivity index (SI) of 0.69 calculated as the $CC_{50}/EC_{90}$ ratio was not statistically different from previous experiments with ribavirin.

TABLE 1

Ribavirin

|  | Exp. 1 | Exp. 1 | ave. |
|---|---|---|---|
| $Y = Y_o + ae^{[-0.5(in(X-Xo)/b)\#2]}$ | | | |
| $EC_{Ribavirin}$ | 6.9 μM | 6.5 μM | 6.7 μM |
| % reduction | 35.5% | 35.3% | 35.4% |
| $Y = Y_o + a/[1 + (X/X_o)^b]$ | | | |
| $EC_{90}$ | 5.96 μM | 5.64 μM | 5.8 μM |
| $CC_{50}$ | 3.6 μM | 4.4 μM | 4.0 μM |
| SI | 0.6 | 0.78 | 0.69 |

Derivatives of Andrographolide:

Derivatives of andrographolide in a semi-purified solution for injection is called Chung-Hu-Ning and was supplied by Yi-Bin Pharmaceuticals (Yibin, Sichuan, PRC). The solution of Chuan-Hu-Ning was tested for antiviral potential in the BVDV in vitro assay system.

Figure 2:
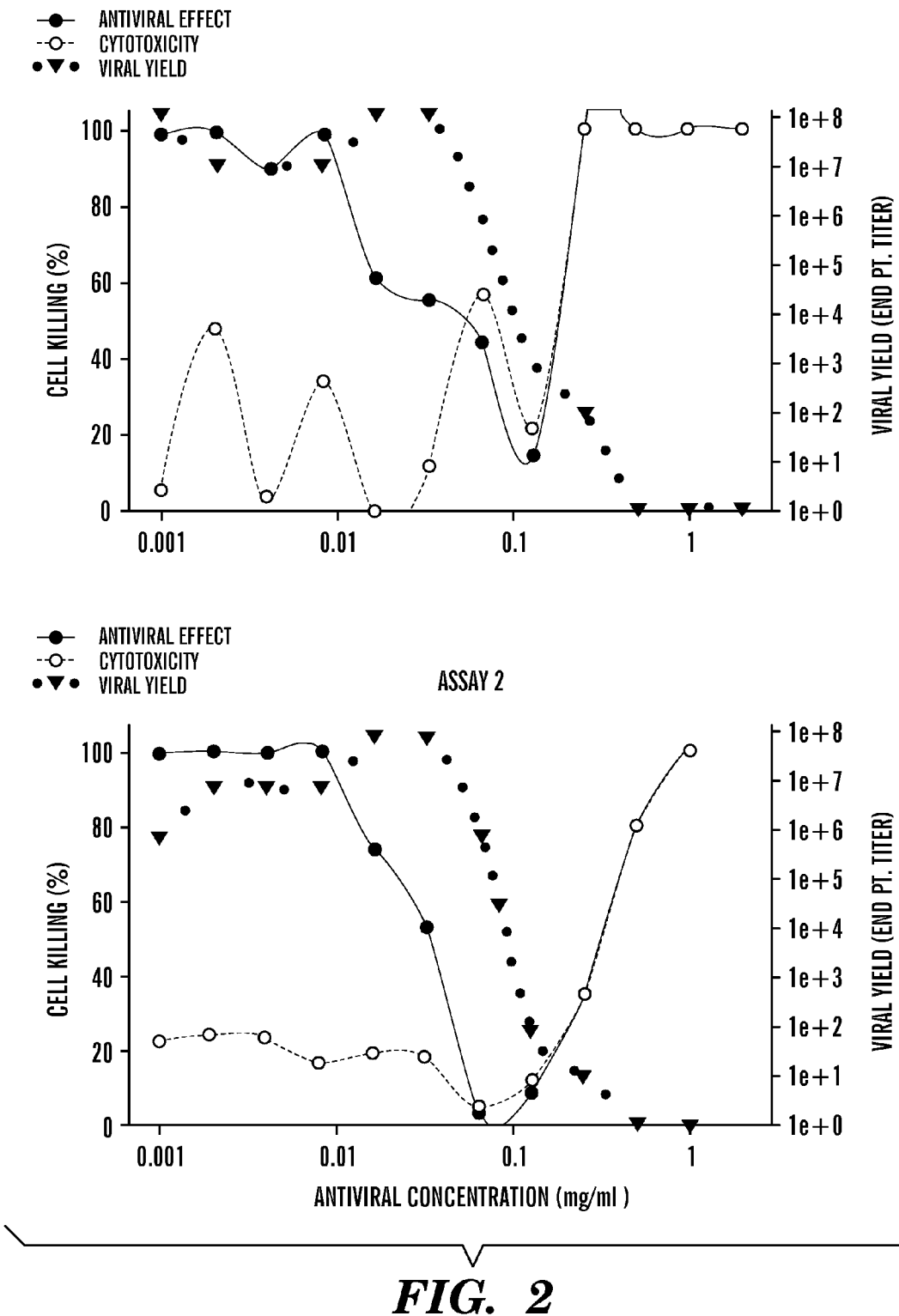
FIG. 2 is a set of line graphs demonstrating the effect of andrographolide derivatives on BVDV cell killing and viral yield after infection of bovine uterine cells. NCL cells were plated at a density of $2 \times 10^4$ cells/well (0.38 cm$^2$) and half the culture plate was inoculated with cpBVDV (m.o.i.=0.01). Infected and uninfected cells were treated with andrographolide derivatives over a range of 2 mg/ml 0.976 µg/ml, for 3 days, followed by methylene blue assay to measure cell numbers. Results of two independently run experiments are shown. Cell killing (%)=[(cell number in uninfected, untreated controls) (cell numbers after BVDV infection with drug treatment or drug treatment alone)]÷(total number of cells in uninfected, untreated controls) at day 3 of assay. Viral yield from BVDV infected cells with drug treatment were determined by infecting fresh cultures with serial 10-fold dilutions of medium collected on day 3 of assay. An end-point titer was measured by methylene blue assay 5 days after infection. A peak, log normal, 4 parameter equation was used to calculate the drug concentration which had the maximal effect toward reducing cell killing due to BVDV infection. A sigmoidal, logistic, 4 parameter equation was used to calculate the drug concentration at which 50% of uninfected cells were killed and the drug concentration which reduced viral titers by 90%.

Experimental data were obtained from two independent assays with ribavirin as a control. Cell killing was normalized to 100% of the control wells to allow comparison between assays. Antiviral effect, cytotoxicity, and reduction in viral yield by the andrographolide derivative for both assays are shown graphically in FIG. 2 The andrographolide derivative exhibited an effective concentration inhibiting 50% of viral-induced cell killing ($EC_{50}$) of 0.031 mg/ml, an effective concentration that reduced virus recovered in the supernatant at the end of the 3 day treatment period by 90% ($EC_{90}$) and a cytotoxic concentration that killed 50% of cells ($CC_{50}$) of 0.27 mg/ml. The selectivity index (SI) of 4.8 was calculated as the $CC_{50}/EC_{90}$ ratio (Table 2).

TABLE 2

Andrographolide Derivative (cmpd 3)

|  | Exp. 1 | Exp. 1 | ave. |
|---|---|---|---|
| $Y = Y_o + ae^{[-0.5(in(X-Xo)/b)\#2]}$ | | | |
| $EC_{50}$ | 0.031 mg/ml | 0.030 mg/ml | 0.031 mg/ml |
| % reduction | 35.5% | 35.3% | 35.4% |
| $Y = Y_o + a/[1 + (X/X_o)^b]$ | | | |
| $EC_{90}$ | 5.96 μM | 5.64 μM | 5.8 μM |
| $CC_{50}$ | 0.20 mg/ml | 0.33 mg/ml | 0.27 mg/ml |
| SI | 3.3 | 6.5 | 4.8 |

Ribavirin, in this assay, exhibited a selectivity index (SI) of 0.69. The derivatives of andrographolide exhibited the following antiviral profile; $CC_{50}$ 0.27 mg/ml, $EC_{50}$ 0.031 mg/ml, and $EC_{90}$ 0.056 mg/ml, yielding a SI of 4.8. Other in vitro assays using BVDV have been shown to be applicable for examination of the antiviral action of nucleoside analogs, natural or recombinant proteins, and synthetic polymers (Zitzmann, N., et al., *Proceedings of the National Academy of Science*, 96(12), 11878-11882, 1999). The nature of the general BVDV assay allows for further delineation into the specific mode of antiviral action exhibited by an individual compound.

Example 2B

Several herbal formulations and pure chemicals, along with a number of pure, putative antiviral compounds described by Schuppan et al. *Hepatology* 30:1099-1104, 1999 were analyzed using the viral assay. Herbal extracts were prepared as described according to known methods. Several herbal extracts as well as andrographolide derivatives exhibited reduction in progeny viral yield that was associated with cytotoxicity of the extract which resulted in complete cell killing and were not dose dependent. (Table 3)

TABLE 3

| Herbal formulations and protein/ andrographolide derivative | Antiviral Activity Inhibition of | | Chemical Compounds | Antiviral activity Inhibition of | |
|---|---|---|---|---|---|
|  | viral-induced cell killing | viral yield |  | viral-induced cell killing | viral yield |
| Yi Gan Kang | +/− | − | Glycyrrhizin | − | − |
| Se Ga Nuo | − | − | Castanospermine | − | − |
| San Han Jin Re | − | − | Amandatine | − | − |
| GAL | − | − | α-Lipoic acid | + | − |
| OLE | +/− | − | N-acetylcysteine | − | − |
| andrographolide derivative (cmpd 3) | +++ | +++ | Mycophenolic acid | + | − |
| Interferon-α | ++ | + | Ribavirin | ++ | + |

Figure 3A:
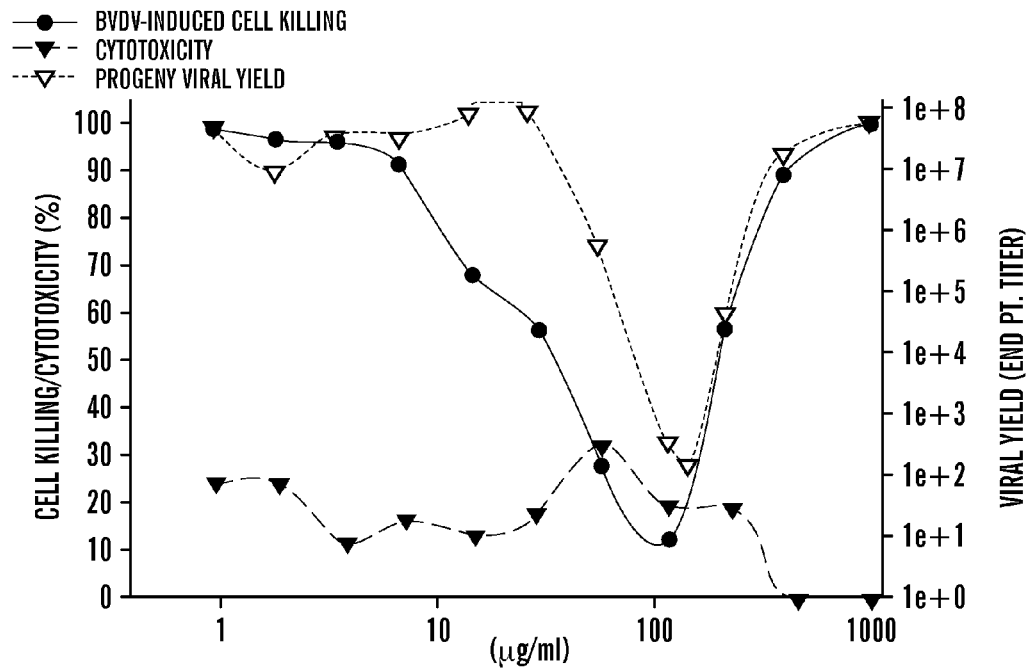
FIG. 3A is a line graph demonstrating the effect of andrographolide derivatives on BVDV cell killing, viral yield, and cytotoxicity after infection of bovine uterine cells. A bovine uterine cell line infected with BVDV was used to assay the antiviral potential of andrographolide derivatives as described in Example 2.

The andrographolide derivative exhibited potent antiviral activity against BVDV (FIG. 3A). There was a definitive dose dependent reduction in progeny virus yields between the concentrations of 32-250 μg/ml, with calculated $_tEC_{90}$=59 μg/ml. Additionally, there was a reduction in viral-induced cell killing between 8-125 μg/ml. with a calculated $_{ck}EC_{50}$=33 μg/ml, approaching 90% reduction at 125 μg/ml. Andrographolide derivative reduced viral yields 7 logs without apparent cytotoxicity. Cytotoxicity associated with the derivative was observed at concentrations greater than 150 μg/ml, with a calculated $CC_{50}$=226 μg/ml.

Figure 3B:
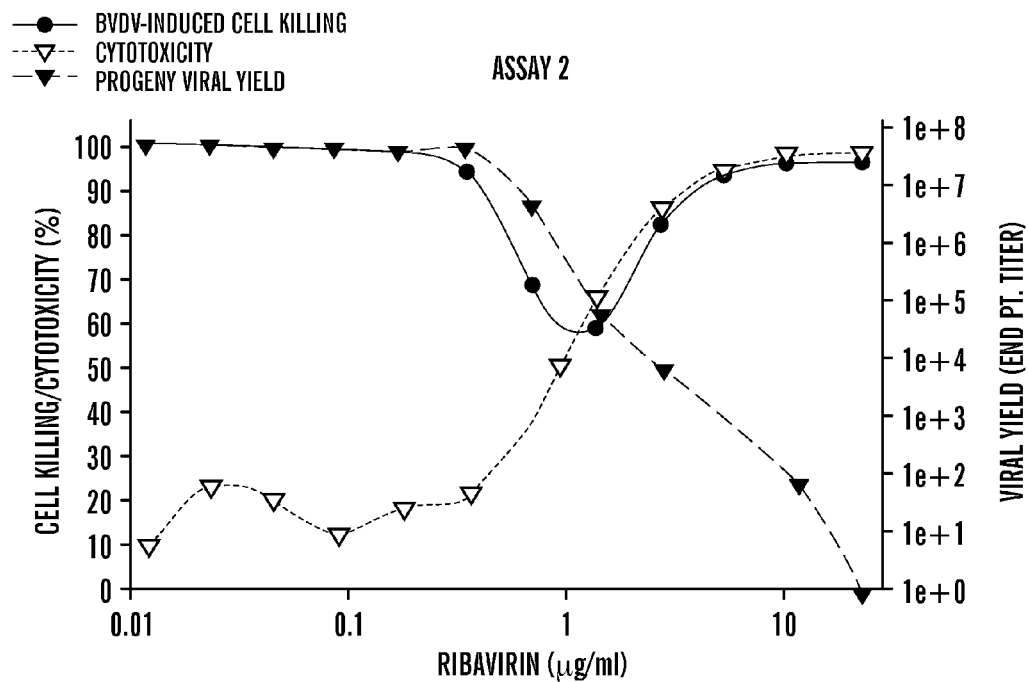
FIG. 3B and FIG. 3C are line graphs demonstrating cell killing, viral yield, and cytotoxicity of ribavirin and interferon-α respectively using the same assay.
Figure 3C:
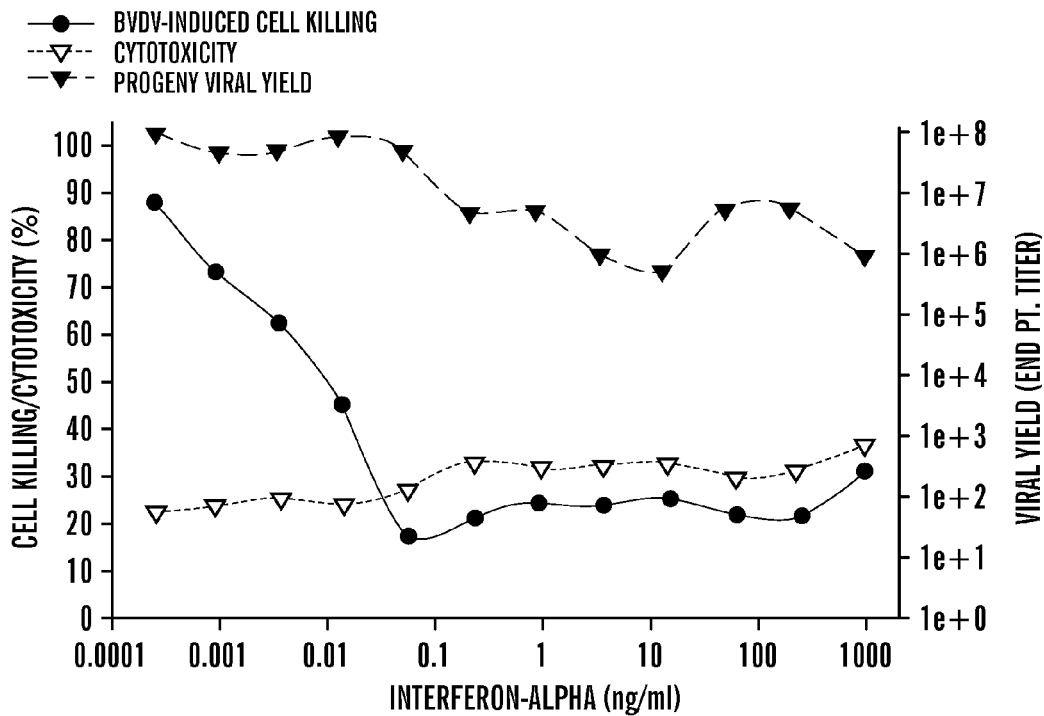
Figure 4A:
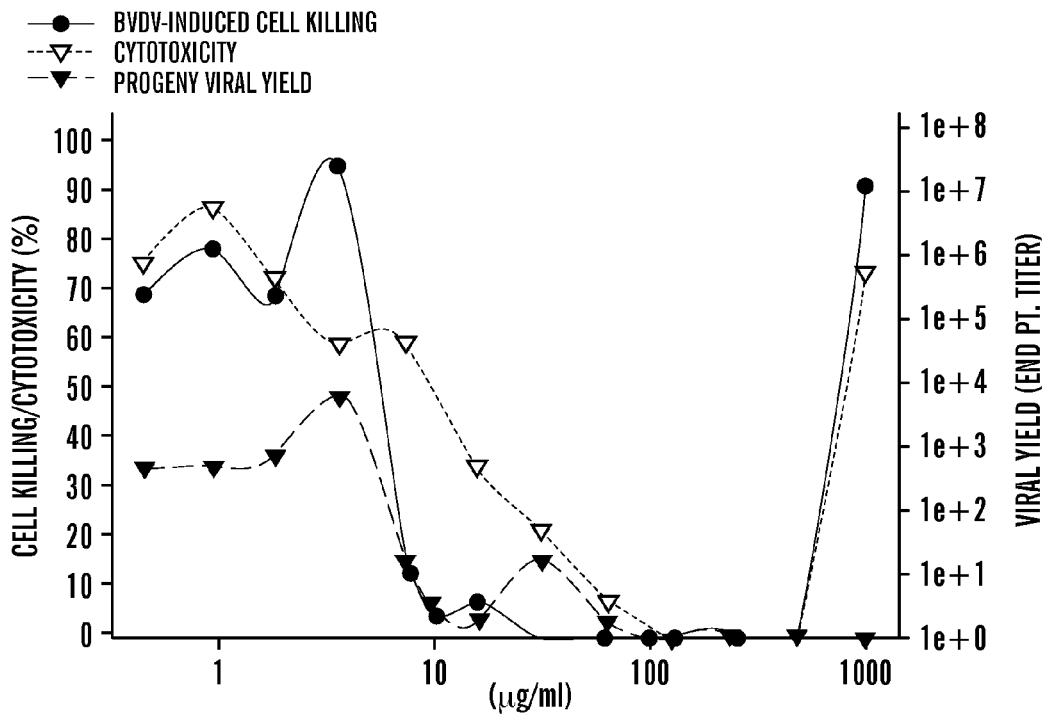
FIG. 4A is a line graph demonstrating the effect of andrographolide derivatives on cell killing, viral yield, and cytotoxicity in WCH-8 cells. WCH-8 cells were inoculated with a cytopathogenic isolate of BVDV. Cytopathogenic effects (CPE) were evident in the woodchuck hepatic cell lines 5 days post infection. Progeny virus was detected in the supernatant 3 days post infection and viral titers of $1.5 \times 10^5$ and $2 \times 10^6$ TCID/ml were produced in cultures for over 3 weeks.
Figure 4B:
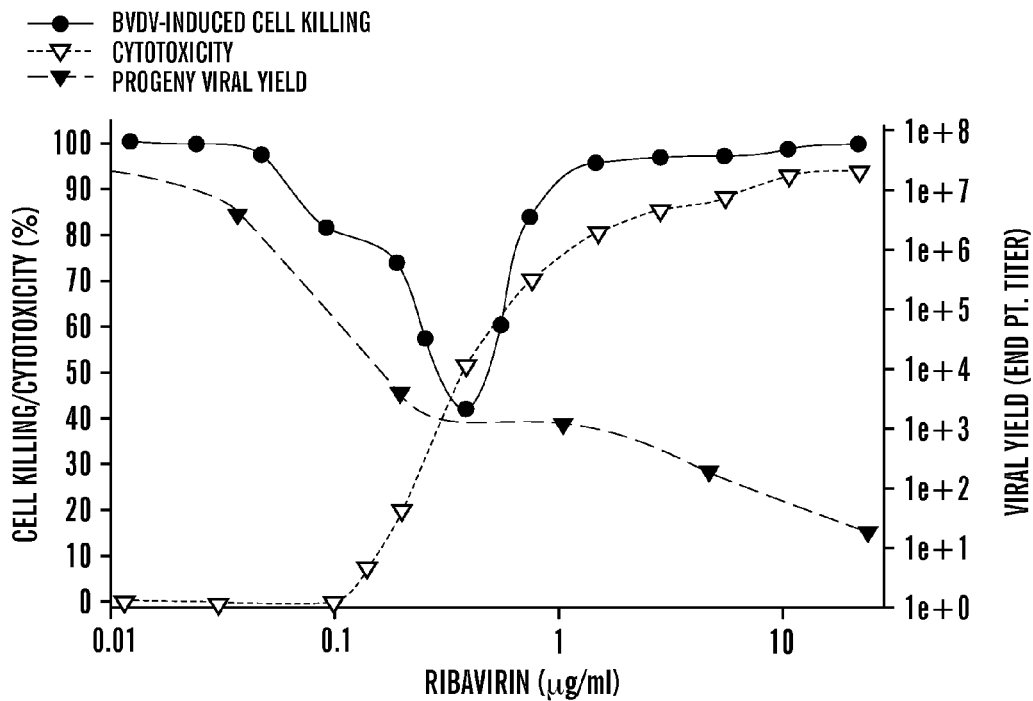
FIGS. 4B and 4C are line graphs demonstrating similar effects of ribavirin and interferon-α respectively using the same assay.
Figure 4C:
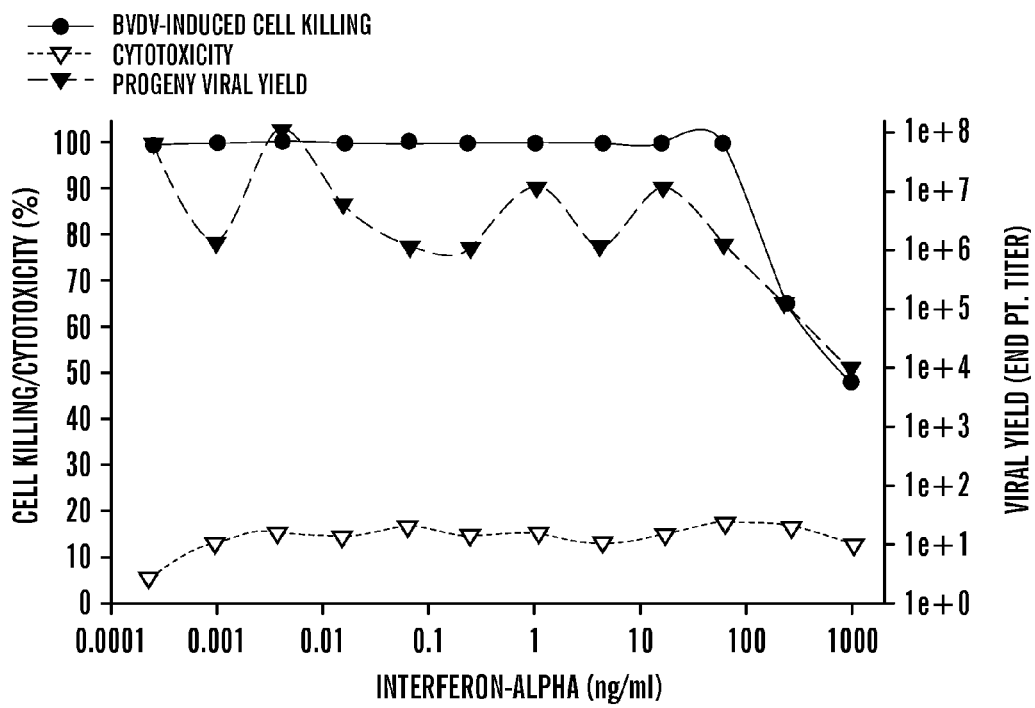
Figure 5A:
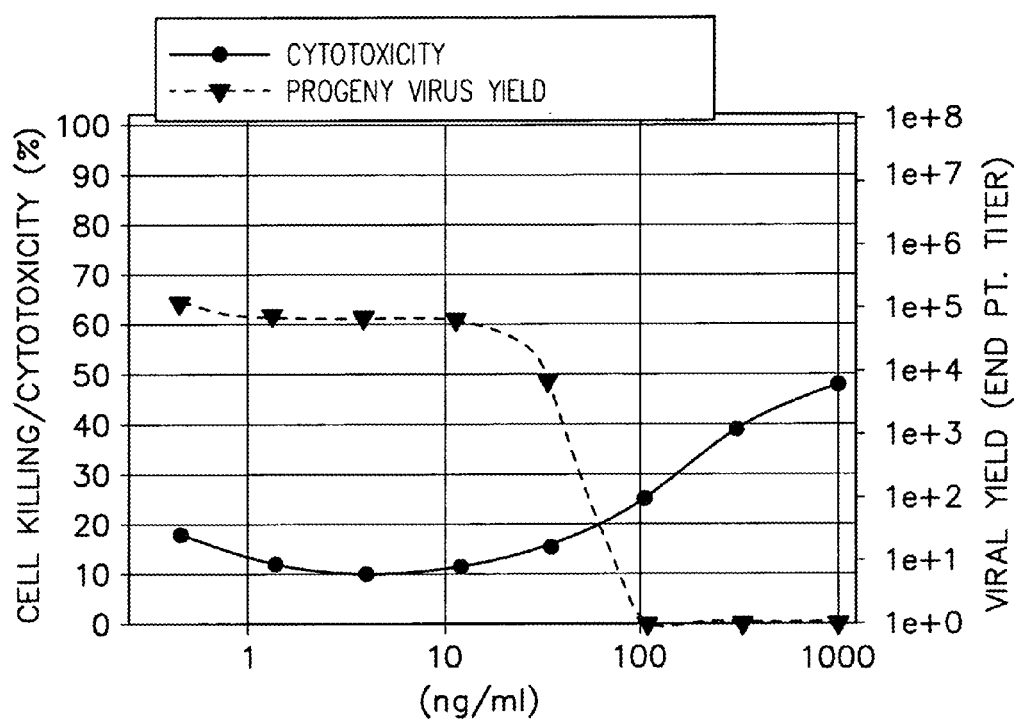
FIG. 5A is a line graph demonstrating the effect of andrographolide derivatives on cytotoxicity and viral yield in woodchuck primary hepatocytes. Woodchuck primary hepatocytes were inoculated with a cytopathogenic isolate of BVDV. No apparent CPE was observed after BVDV infection in woodchuck primary hepatocytes. Progeny virus was detected in the supernatant 3 days post infection and viral titers of $1.5 \times 10^5$ and $2 \times 10^6$ TCID/ml were produced in cultures for over 3 weeks.
Figure 5B:
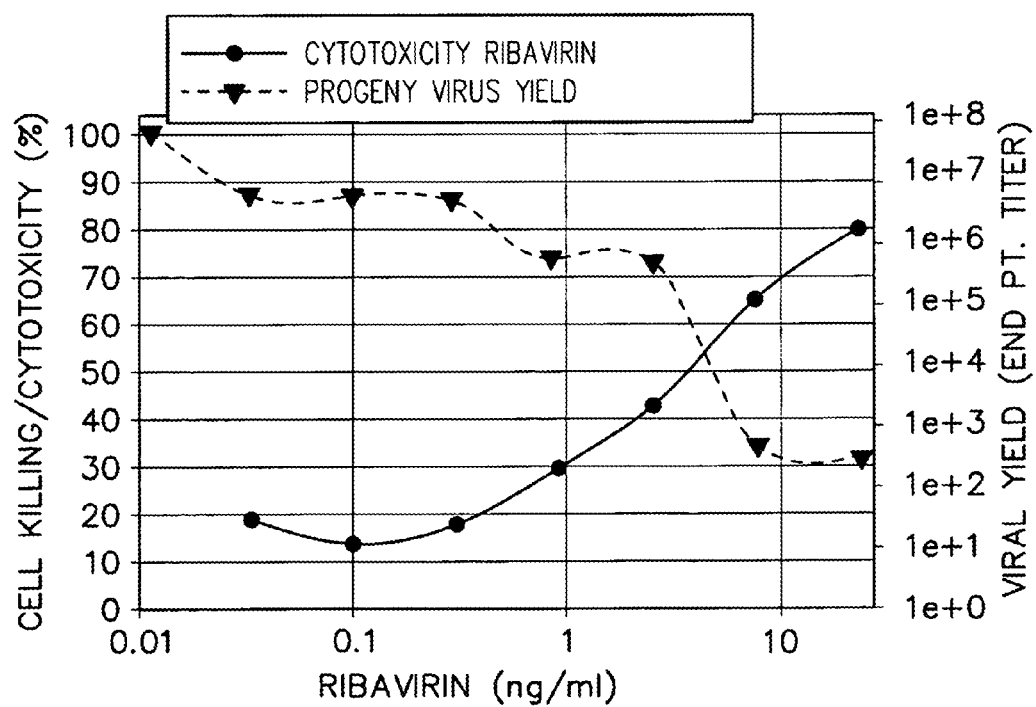
FIGS. 5B and 5C are line graphs demonstrating the effects of ribavirin and interferon-α on cytotoxicity and viral yield using the same assay.
Figure 5C:
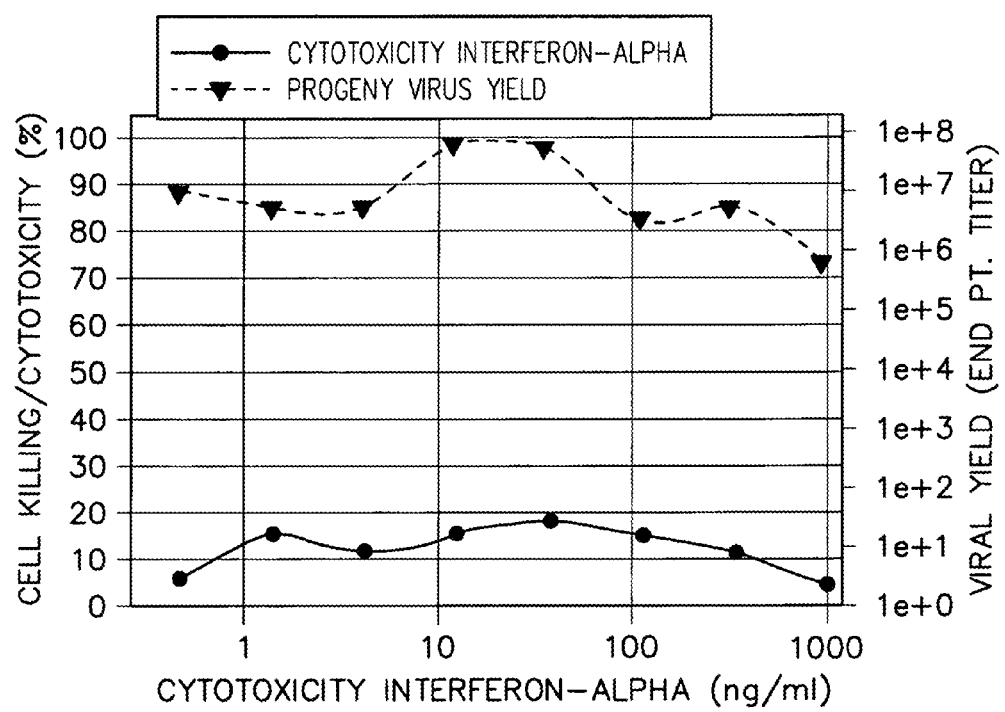
Figure 6A:
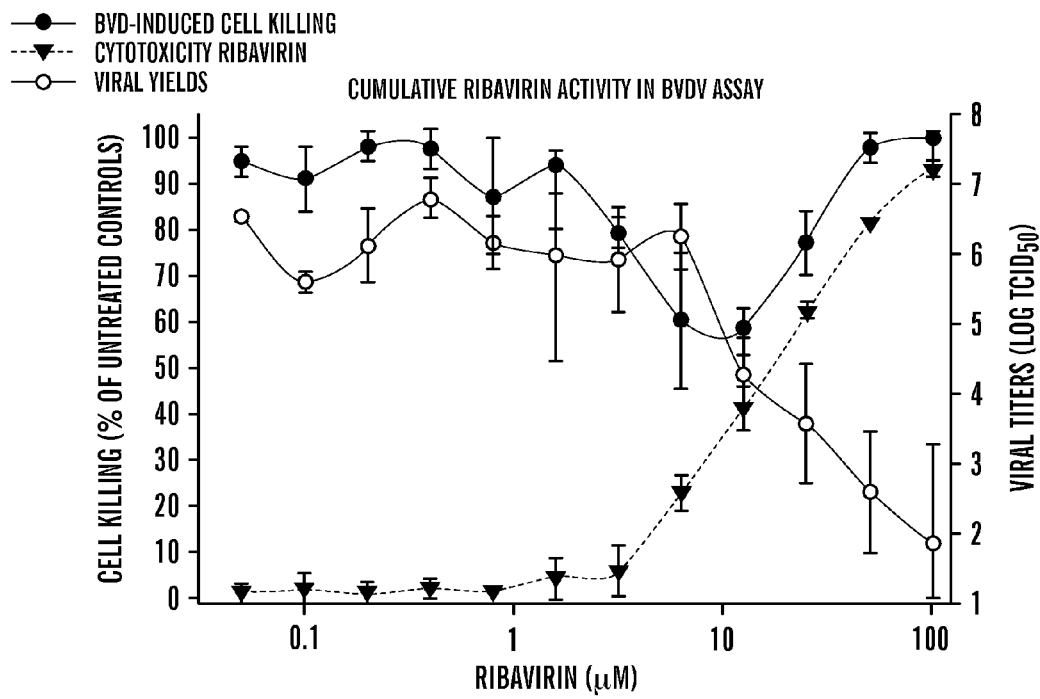
FIG. 6A is a line graph demonstrating the cumulative ribavirin activity in a BVDV assay as a positive control.
Figure 6B:
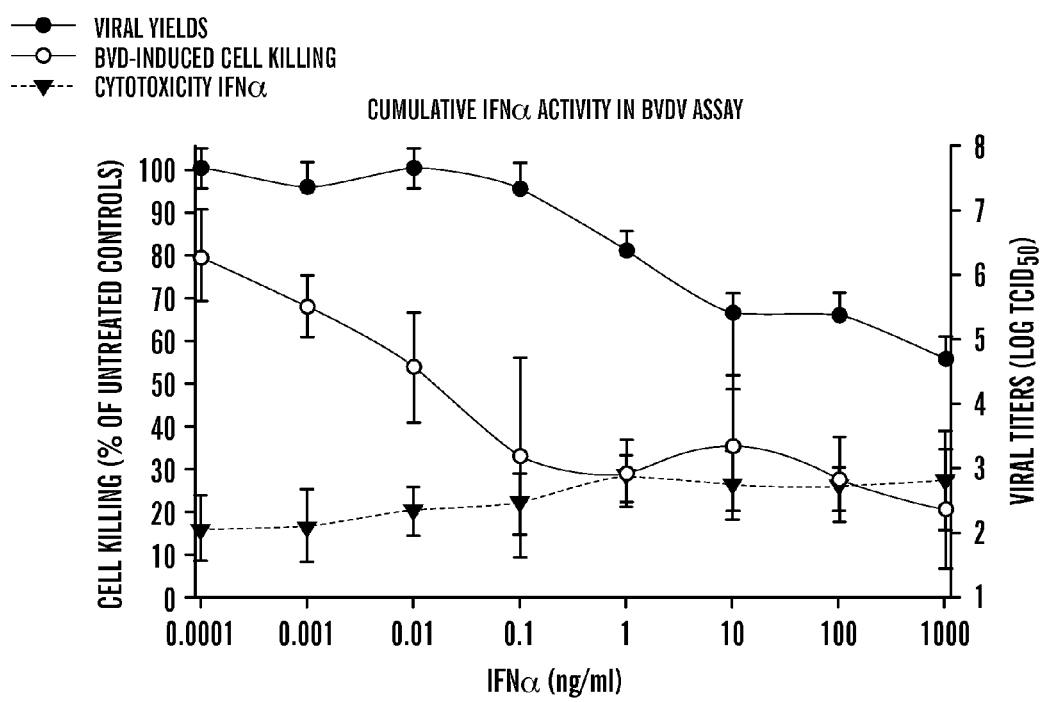
FIG. 6B is a line graph demonstrating the cumulative α-interferon activity in a BVDV assay also as a positive control.
Figure 7A:
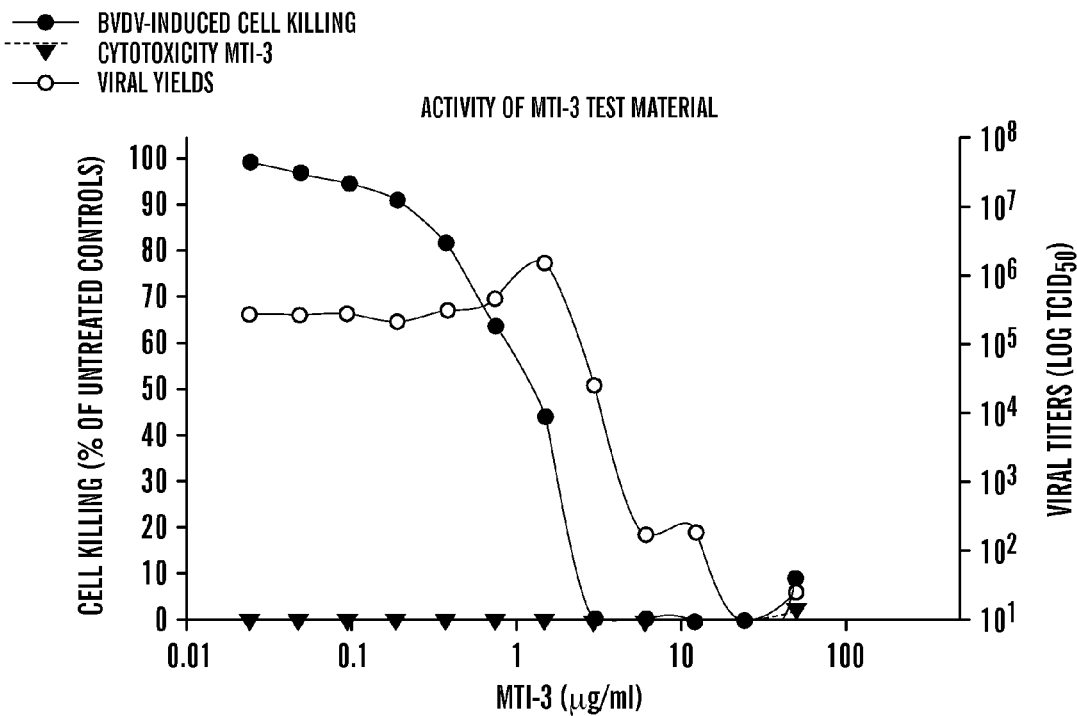
FIG. 7A is a line graph regarding the activity of an andrographolide analog of the present invention in a single BVDV assay.
Figure 7B:
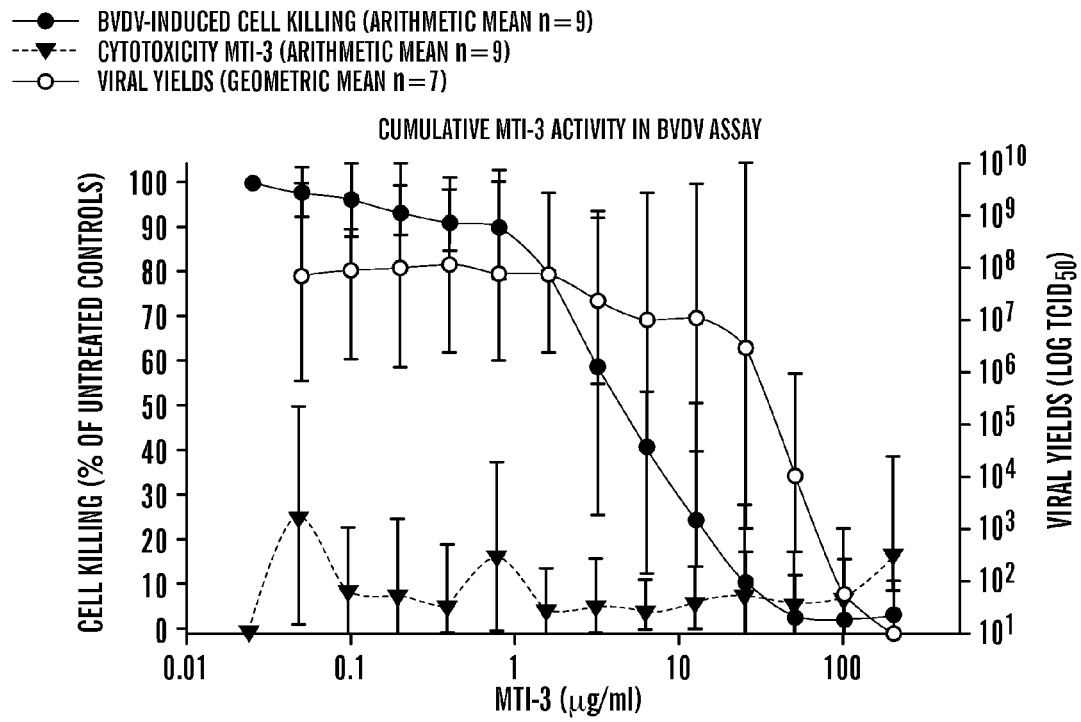
FIG. 7B is a line graph demonstrating the cumulative activity of an andrographolide analog of the present invention, averaging nine separate assay results.
Figure 8A:
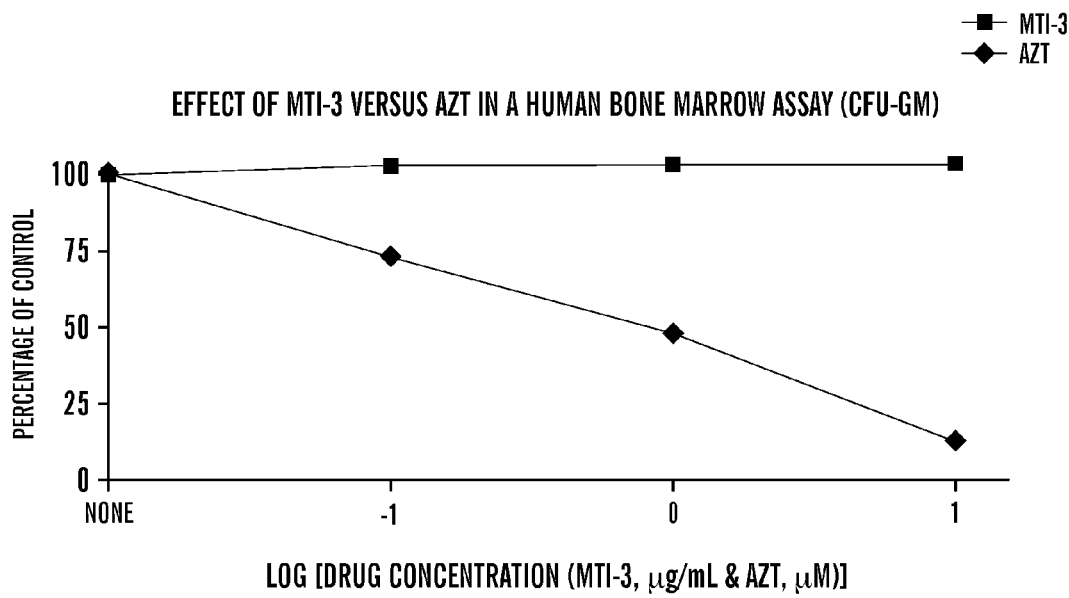
FIG. 8A is a line graph of human bone marrow toxicity performed in soft agar with human recombinatnt granulocyte/macrophage colony-stimulating factor comparing a mixture of succinic acid esters of andrographolide (MTI-3; an injectable form of an andrographolide derivative contained in an *Andrographis paniculata* extract from Chuan-Hu-Ning; Yi-Bin Pharmaceuticals, Wuliangye Co. Ltd., Yibin, Sichaun, PR China) and AZT as a control.
Figure 8B:
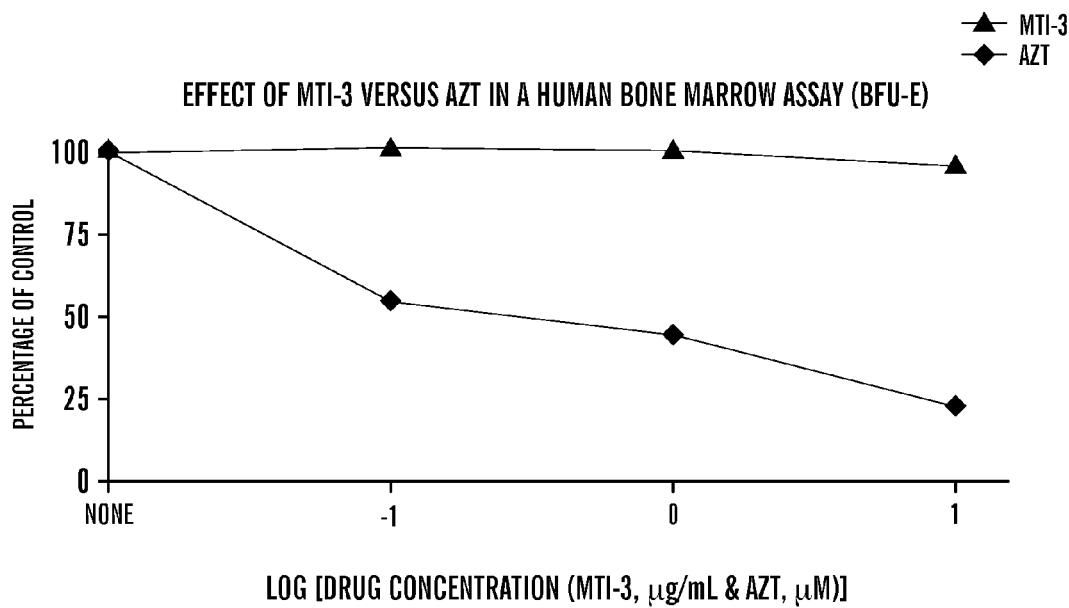
FIG. 8B is a line graph of human bone marrow toxicity performed in a methylcellulose matrix with erythropeoetin comparing MTI-3 and AZT as a control.

In comparison, ribavirin reduced viral yields over a range of 0.76-12 μg/ml, with a calculated $_tEC_{90}$=0.76 μg/ml (FIG. 3B). However, the maximal reduction in viral-induced cell killing was only 40% with an extrapolated $_{ck}EC_{50}$=1.3 μg/ml. This value was near the midpoint of drug cytotoxicity, calculated as $CC_{50}$=1.1 μg/ml. IFN-α showed only minimal effectiveness toward reduction in viral yields, calculated $_tEC_{90}$=0.15 μg/ml (FIG. 3C). There was a substantial reduction in viral-induced cell killing between 0.1-1000 ng/ml, calculated $_{ck}EC_{50}$=0.0074 mg/ml, and did not exhibit cytotoxicity over the range tested. Among the tested compounds, the andrographolide derivative demonstrated a higher selectivity index ($CC_{50}/EC_{90}$=3.8) than ribavirin (0.85), though less than IFN-α (6667) (Table 4).

TABLE 4

| Antiviral | $_{ck}EC_{50}$ | $_tEC_{90}$ | $CC_{50}$ | S.I. |
|---|---|---|---|---|
| andrographolide derivative (cmpd 3) | 33 μg/ml | 59 μg/ml | 226 μg/ml | 3.8 |
| ribavirin | 1.3 μg/ml | 0.76 μg/ml | 1.1 μg/ml | 0.895 |
| interferon-α | 0.0074 ng/ml | 0.15 μg/ml | ≧1000 ng/ml | 6667 |

The andrographolide derivative showed maximal reduction on viral-induced cell killing of 90% ($_{ck}EC_{50}$=33 μg/ml), which was greater than the 40% reduction by ribavirin ($_{ck}EC6_{50}$=0.76 μg/ml). Although IFN-α showed an 80% reduction in viral-induced cell killing over a broader range ($_{ck}EC_{50}$=0.0074 ng/ml) it demonstrated only a 2 log reduction in viral yields. The effective concentration at which the andrographolide derivative reduced progeny virus yields by 7 logs was removed from the drugs cytotoxicity (S.I.=3.8). The effective concentration at which ribavirin reduced viral yields closely overlapped the drugs cytotoxicity (S.I.=0.85). IFN-α exhibits a poor reduction on viral yield, but shows a broad effect on viral-induced cell killing (S.I.=6667). These results suggest that the andrographolide derivative will exert an antiviral effect in persistent BVDV-infected calves.

Example 3

Woodchuck Hepatocyte Model

The mechanism of through which andrographolide derivatives (thought to include a mixture of succinic acid esters) inhibit BVDV replication was investigated in woodchuck hepatocytes. Woodchuck primary hepatocyte cultures and hepatic cell lines were inoculated with a cytopathogenic isolate of BVDV. Cytopathogenic effects (CPE) were evident in the woodchuck hepatic cell lines 5 days post infection. No apparent CPE, however, was observed after BVDV infection in woodchuck primary hepatocytes. Progeny virus was detected in the supernatant 3 days post infection and viral titers of $1.5 \times 10^5$ and $2 \times 10^6$ TCID/ml were produced in cultures of woodchuck primary hepatocytes and hepatic cell lines, respectively, for over 3 weeks. The expression of non-structural protein p80 (NS3) which is associated with replication of cytopathogenic strains of BVDV, was detected in homogenates of BVDV infected woodchuck cell cultures with or without CPE, but not in control cultures. Full-length viral genomes were detected in RNA extracted from infected woodchuck hepatocytes.

Figures 9A, 9B:
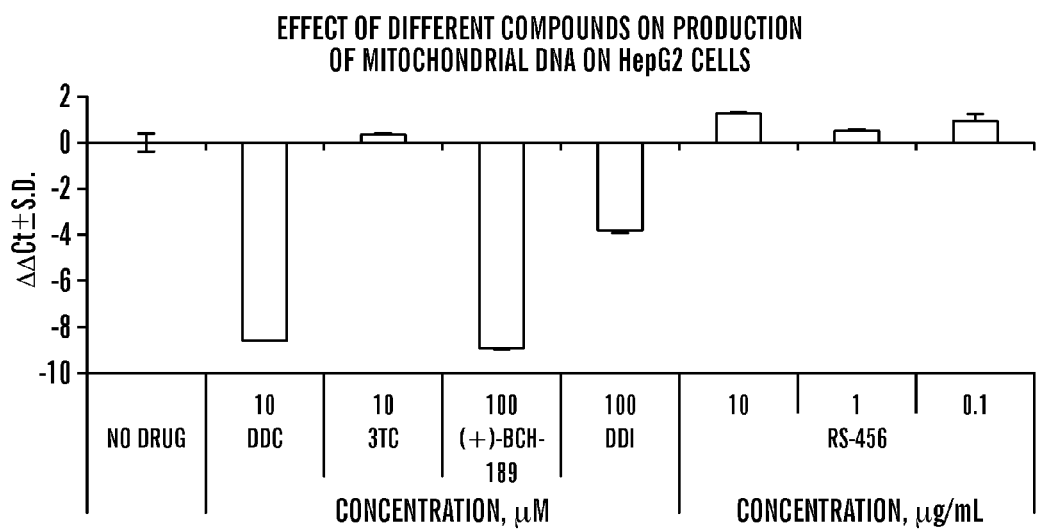
FIG. 9A is a chart showing the effect of different drugs on lactic acid production and mitochondrial DNA production in HepG2 cells.
FIG. 9B is a bar graph of the ratio of mitochondrial DNA to ribosomal DNA in HepG2 cells treated with different drugs. DDC, zalcitabine; 3TC, lamivudine; (+)-BCH-189, and DDI, didanosine were included as controls. ΔΔCt is COXII Ct—ribosomal RNA Ct—no drug control ΔCt. The ratios were determined using real time-PCR.

Andrographolide derivative (cmpd 3), ribavirin, and IFN-α were tested for antiviral activity against BVDV-infected woodchuck primary hepatocytes and hepatic cell lines. Effective and cytotoxic concentrations were evaluated by similar methods describe in Examples 1 and 2.

Andrographolide derivative (cmpd 3) as well as both ribavirin and IFN-α demonstrated antiviral activity against BVDV in both woodchuck hepatic cells (WCH-8) and primary hepatocyte cultures. In WCH-8 cells there was a pronounced separation between the effective antiviral concentrations of andrographolide derivatives toward reduction of viral yield (${}_{t}EC_{90}$=3.8 μg/ml) and viral-induced cell killing (${}_{ck}EC_{50}$=6 μg/ml) versus cytotoxicity ($CC_{50}$=878 μg/ml) (FIG. 4A). Identical treatment of WCH-8 cells with ribavirin showed an overlap in the reduction of viral yield (${}_{t}EC_{90}$=0.38 μg/ml), viral induced cell killing (${}_{ck}EC_{50}$=0.27 μg/ml) and its cytotoxicity ($CC_{50}$=0.35 μg/ml) (FIG. 4B). In WCH-8 cells treated with IFN-α the antiviral effect on viral yield (${}_{t}EC_{90}$=64 ng/ml) and viral-induced cell killing (${}_{ck}EC_{50}$=288 ng/ml) was observed at the high end of drug concentrations tested. No cytotoxicity was observed up to a dose of 1000 ng/ml (FIG. 4C). The results of these experiments are in Table 5 and the selectivity index calculated as 232, 9.2, and 15.6 for andrographolide derivatives, ribavirin, and INF-α respectively.

TABLE 5

| Antiviral | ${}_{ck}EC_{50}$ | ${}_{t}EC_{90}$ | $CC_{50}$ | S.I. |
|---|---|---|---|---|
| andrographolide derivative | 6.0 μg/ml | 3.8 μg/ml | 878 μg/ml | 232 |
| ribavirin | .27 μg/ml | 0.038 μg/ml | 0.35 μg/ml | 9.2 |
| interferon-α | 288 ng/ml | 64 ng/ml | ≧1000 ng/ml | 15.6 |

In woodchuck primary hepatocytes treated with andrographolide derivatives a reduction in the viral yield (${}_{t}EC_{90}$=35 μg/ml) was observed at concentrations below the drug's cytotoxicity ($CC_{50}$=1000) (FIG. 5A). In woodchuck primary hepatocytes BVDV-induced cell killing is not evident. Identical primary hepatocyte cultures treated with ribavirin show the reduction of viral yield (${}_{t}EC_{90}$=2.9 μg/ml) at concentrations approximating the drug's cytotoxicity ($CC_{50}$=4 μg/ml) (FIG. 5B). IFN-α treatment of BVDV-infected hepatocytes had minimal effect on reduction of viral yields (${}_{t}EC_{90}$=825 ng/ml), although no cytotoxicity was observed over the range tested (FIG. 5C). The results of these experiments are presented in Table 6 and the selective index in this assay were calculated as 29, 1.4, and 1.1 for andrographolide derivatives, ribavirin, and IFN-α respectively.

TABLE 6

| Antiviral | ${}_{ck}EC_{50}$ | ${}_{t}EC_{90}$ | $CC_{50}$ | S.I. |
|---|---|---|---|---|
| andrographolide derivative | *ND | 35 μg/ml | 1000 μg/ml | 29 |
| ribavirin | ND | 2.9 μg/ml | 4 μg/ml | 1.4 |
| interferon-α | ND | 825 ng/ml | ≧1000 ng/ml | 1.1 |

*ND—not determined.
BVDV-induced cell killing is not evident in primary hepatocytes.

Andrographolide derivatives exhibited antiviral potential (S.I. 29) in BVDV-infected woodchuck primary hepatocytes and hepatic cell lines, when compared to the antiviral potential of ribavirin (S.I. 1.4) and IFN-α (S.I. 1.1). The reduction of virus replication closely approximates the loss of viable cells due to cell killing by the drug.

Example 4

Bovine Uterine Endometrial Cell Assay

Antiviral activity of the test compounds was assessed in BVDV assay using bovine cell lines generated via immortalization of primary bovine uterine endometrial cells with the SV40 large T antigen in 96-well plates. These cell lines are permissive to cytopathogenic BVDV isolates (Singer and NADL). The assay was optimized such that within 3 days of infection (moi<1), >90% BVDV-induced cell killing was measured. Upon drug treatment applied fresh each day for 3 sequential days, the assay determined the compounds effective concentration to inhibit BVDV-induced cell killing by 50% ($EC_{50}$) and at which concentration 50% of normal, uninfected cells are killed due to the cytotoxic effects of the drug ($CC_{50}$). BVDV in the culture media collected on day 3 of drug treatment is titered on fresh endometrial cell cultures to determine reduction in progeny viral yields by 90% ($EC_{90}$). Linear regression equations are employed to determine effective concentrations (SigmnaPlot8.0; SPSS Scientific, Chicago, Ill.). Ribavirin (Virazole; Viratek, Inc., Covina, Calif.) and IFN-α (rHuB/DIFN; Novartis, Basel, Switzerland) serve as positive antiviral controls.

FIGS. 6A and 6B summarize the BVDV assay results with ribavirin and IFN-alpha, respectively, which have been used as positive controls. FIGS. 7A and 7B summarize the BVDV assay results with MTI-3. The $EC_{90}$ was about 2.5 μg/mL and the toxicity was negligible at 50 μg/mL, the highest concentration of the mixture of succinic acid esters of andrographolide tested.

Example 5

Mitochondrial DNA Levels

Mitochondrial toxicity was measured using relative ratios of mitochondrial DNA to ribosomal DNA. These were measured using the ratio of COXII ribosomal RNA as measured by real-time PCR. Hep G2 cells were exposed for 14 days to 10, 1 nd 0.1 ug/ml of MTI-3 or control drugs (DDC, 3TC, (+)-BCH-189, or ddI) at 10 or 1000 uM. The results are shown in FIG. 9B. Lactic acid production was also measured in these cells as a toxic byproduct. The results are shown in FIG. 9A.

Example 6

SEAP Assay

HCV replicon—SEAP (secreted alkaline phosphatase) cell lines have been described previously. Low passage cell stocks of cell lines stored frozen (−160° C.) were used in the assays. Serial dilutions of test compounds were made from initial stocks and each concentration plated in 96-well plates. Low passage HCV replicon-bearing cells were then trypsinized, counted and seeded into the wells. The plates were incubated at 37° C. in a $CO_2$ incubator for 4 days. The culture supernatant was then removed from each well and heat inactivated for 30 min at 65° C. SEAP activity was measured and EC50 values calculated by comparing SEAP present in drug-treated and untreated wells. Cytotoxicity produced by compounds during screening was evaluated by MTT assay at the end of the incubation period.

Total RNA was isolated from cultures of the HCV replicon cells and the amount was based upon the GAPDH levels observed in the RT-PCRs. Growth medium from each well was aspirated prior to the addition of lysis solution followed by vigorous pipetting. Each lysate was processed using DNase I treatment. Total RNA was eluted into orgainic carbon-free water and converted into cDNA enzymatically. Real-time PCR reactions were performed using primers for HCV designed to recognize a conserved region of the 5'-non-translated region common to all HCV genotypes. The primers for human GAPDH were designed to allow co-amplification of the two targets in multiplex fashion. (Bourne N, Pyles R B, Yi M, Veselenak R L, Davis M M, Lemon S M Screening for hepatitis C virus antiviral activity with a cell-based secreted alkaline phosphatase reporter replicon system. Antiviral Res. 2005; 67:76-82. The results from these assays are shown in Table 5.

TABLE 5

Anti-HCV Assay of Compounds using SEAP Reporter Method

| | SEAP, $EC_{50}$ | MTT, $IC_{50}$ | SI |
|---|---|---|---|
| SEAP/MTT primary screen subgenomic 1b Strain N | | | |
| 2'-MeC | 25.1 µM | >100.0 µM | >3.9 |
| MTI-3 | 8.5 µg/ml | >100.0 µg/ml | >11.7 |
| Extract* | >100.0 µg/ml | >100.0 µg/ml | — |
| Intron | 6.3 I.U. | >500.0 I.U. | >79.2 |
| SEAP/MTT primary screen subgenomic 1a | | | |
| 2'-MeC | 61.6 µM | >100.0 µM | >1.6 |
| MTI-3 | 17.4 µg/ml | >100.0 µg/ml | >5.7 |

TABLE 5-continued

Anti-HCV Assay of Compounds using SEAP Reporter Method

| | SEAP, $EC_{50}$ | MTT, $IC_{50}$ | SI |
|---|---|---|---|
| Extract* | >100.0 µg/ml | >100.0 µg/ml | — |
| Intron | 14.4 I.U. | >500.0 I.U. | >34.6 |

Example 7

Anti-HCV Activity of Compounds in Replicaon-Transfected Huh-7 Cell Lines

HCV-replicon RNA-containing Huh-7 cells (Apath, LLC, St. Louis, Mo.) were maintained in exponential growth. Cells were seeded in a 96-well plate and test compounds were added following seeding. After 96 h of incubation, total cellular RNA was isolated and HCV replicon RNA and an internal control were amplified using a single-step multiplex reverse transcription-PCR protocol. The cellular toxicity against Huh-7 and HepG2 cells was measured at the end of incubation and the concentration resulting in 50% reduction in cell growth ($CC_{50}$) was determined. S(Stuyver U J, McBrayer T R, Whitaker T, Tharnish P M, Ramesh M, Lostia S, Cartee L L, Shi J, Hobbs A, Schinazi R F, Watanabe K A, Otto M J. Antimicrob Agents Chemother. 2004; 48:651-4. Results on these assays are shown in FIG. 10.

This invention has been described with reference to its preferred embodiments. Variations and modifications of the invention, will be obvious to those skilled in the art from the foregoing detailed description of the invention.

What is claimed is:

1. A method for treating a host infected with a BVDV or HCV comprising administering to the host an effective amount of a dehydroandrographolide succinic acid diester of the formula:

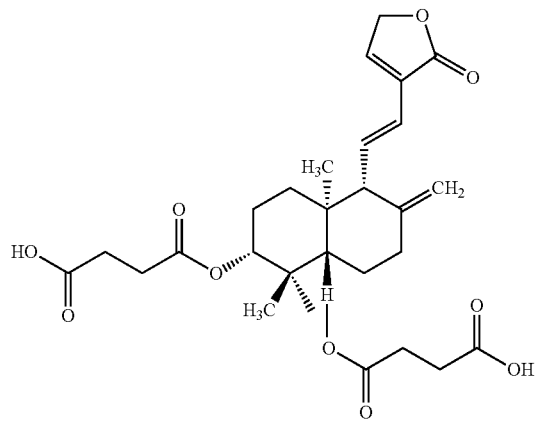

or its pharmaceutically acceptable salt.

2. The method of claim 1, wherein the dehydroandrographolide succinic acid diester is administered in combination or alternation with a second antiviral agent.

* * * * *